US 11,071,865 B2

(12) United States Patent
Klepfer et al.

(10) Patent No.: US 11,071,865 B2
(45) Date of Patent: Jul. 27, 2021

(54) MODE OF OPERATION FOR AN IMPLANTABLE CARDIAC RHYTHM MANAGEMENT DEVICE CO-IMPLANTED WITH A VENTRICULAR ASSIST DEVICE

(71) Applicant: Medtronic, Inc., Minneapolis, MN (US)

(72) Inventors: Ruth N. Klepfer, St. Louis Park, MN (US); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 497 days.

(21) Appl. No.: 15/969,872

(22) Filed: May 3, 2018

(65) Prior Publication Data

US 2019/0336767 A1 Nov. 7, 2019

(51) Int. Cl.
*A61N 1/36* (2006.01)
*A61N 1/362* (2006.01)
(Continued)

(52) U.S. Cl.
CPC ......... *A61N 1/3629* (2017.08); *A61M 60/148* (2021.01); *A61N 1/3621* (2013.01);
(Continued)

(58) Field of Classification Search
CPC ............... A61N 1/3629; A61N 1/3621; A61N 1/36521; A61N 1/36557; A61N 1/36564;
(Continued)

(56) References Cited

U.S. PATENT DOCUMENTS 5,156,148 A 10/1992 Cohen
6,898,462 B2 5/2005 Rock et al.
(Continued)

FOREIGN PATENT DOCUMENTS

DE 202017001760 U1 5/2017
EP 0280301 A2 8/1988

OTHER PUBLICATIONS

Richardson et al., "Prospective Randomized Evaluation of Implantable Cardioverter-Defibrillator Programming in Patients With a Left Ventricular Assist Device", American Heart Association, 2018, 9 pages.

(Continued)

*Primary Examiner* — Amanda K Hulbert
*Assistant Examiner* — Natasha Patel
(74) *Attorney, Agent, or Firm* — Medtronic, Inc.

(57) ABSTRACT

An implantable cardiac rhythm management medical device is configured to switch from a first operating mode to a second, ventricular assist device operating mode for detecting cardiac arrhythmias and controlling delivery of anti-arrhythmia therapy during the ventricular assist device operating mode. The implantable medical device may receive a command from another medical device indicating co-implantation of a ventricular assist device with the implantable medical device in a patient and switch from the first mode of operating to the second mode of operating in response to receiving the command. Switching from the first mode to the second mode may include adjusting at least one control parameter used for controlling an electrical stimulation therapy deliverable by the implantable cardiac rhythm management medical device.

36 Claims, 9 Drawing Sheets

(51) Int. Cl.
*A61N 1/365* (2006.01)
*A61N 1/372* (2006.01)
*A61N 1/39* (2006.01)
*A61M 60/148* (2021.01)

(52) U.S. Cl.
CPC ..... *A61N 1/36521* (2013.01); *A61N 1/36557* (2013.01); *A61N 1/36564* (2013.01); *A61N 1/36585* (2013.01); *A61N 1/37223* (2013.01); *A61N 1/37247* (2013.01); *A61N 1/37258* (2013.01); *A61N 1/3956* (2013.01); *A61N 1/3987* (2013.01)

(58) Field of Classification Search
CPC ............ A61N 1/36585; A61N 1/37223; A61N 1/37247; A61N 1/37258; A61N 1/3956; A61N 1/3987; A61N 1/056; A61N 1/3688; A61N 1/37235; A61M 1/122
See application file for complete search history.

(56) References Cited

U.S. PATENT DOCUMENTS

| | | |
|---|---|---|
| 7,761,150 B2 | 7/2010 | Ghanem et al. |
| 8,864,644 B2 | 10/2014 | Yomtov |
| 9,042,979 B2 | 5/2015 | Peters et al. |
| 9,433,714 B2 | 9/2016 | Voskoboynikov et al. |
| 9,579,435 B2 | 2/2017 | Yomtov |
| 9,808,637 B2 | 11/2017 | Sharma et al. |
| 9,844,675 B2 | 12/2017 | Hareland et al. |
| 9,855,414 B2 | 1/2018 | Marshall et al. |
| 2008/0269573 A1* | 10/2008 | Najafi .................... A61B 5/076 600/301 |
| 2011/0270331 A1 | 11/2011 | Peters et al. |
| 2012/0310037 A1 | 12/2012 | Choi et al. |
| 2015/0073203 A1* | 3/2015 | Wariar ................ A61M 1/1086 600/17 |
| 2015/0306375 A1 | 10/2015 | Marshall et al. |
| 2016/0158567 A1 | 6/2016 | Marshall et al. |
| 2018/0280599 A1* | 10/2018 | Harjes ................ A61B 5/02405 |

OTHER PUBLICATIONS (PCT/US2019/030101) PCT Notification of Transmittal of the International Search Report and the Written Opinion of the International Searching Authority, dated Jul. 12, 2019, 11 pages.

* cited by examiner

MODE OF OPERATION FOR AN IMPLANTABLE CARDIAC RHYTHM MANAGEMENT DEVICE CO-IMPLANTED WITH A VENTRICULAR ASSIST DEVICE

TECHNICAL FIELD

This disclosure relates to an implantable medical device (IMD) for cardiac rhythm management that is co-implantable with a ventricular assist device (VAD) and configurable for a VAD mode of operation.

BACKGROUND

A VAD is an implantable blood pump that assists an impaired heart by pumping blood to support the workload of the heart. A VAD may be coupled along the arterial system, e.g., between a ventricular chamber and an artery, to pump blood from the ventricle into the arterial system. For example, a left ventricular assist device or LVAD may be coupled between the left ventricle and the ascending or descending aorta. Assistance in pumping blood by a VAD can be provided to a heart failure patient acutely or chronically, as a bridge to heart transplant, as temporary support to allow myocardial recovery, or as a permanent assist device for heart failure patients contraindicated for heart transplant.

A cardiac rhythm management device, such as a pacemaker or an implantable cardioverter defibrillator (ICD) monitors a patient's heart rhythm and provides electrical stimulation therapy, such as bradycardia pacing, cardiac resynchronization therapy (CRT), anti-tachycardia pacing (ATP) or a cardioversion/defibrillation (CV/DF) shock, in response to detecting an abnormal electrical rhythm. ICDs are generally designed to detect life threatening ventricular tachyarrhythmia and rapidly respond to the detection by preparing for and delivering ATP and/or cardioversion or defibrillation shock(s) to prevent sudden cardiac death. Heart failure patients are at risk of sudden cardiac death due to arrhythmia. ICD implantation in heart failure patients reduces the risk of sudden cardiac death. Patients having both a VAD and an ICD may have improved survival.

SUMMARY

The techniques of this disclosure generally relate to an IMD that is co-implantable with a VAD and configurable to operate in a VAD mode for monitoring a patient's cardiac rhythm and/or controlling therapy delivered by the IMD when the VAD is present. The VAD mode may include withholding or delaying a shock therapy that is normally delivered upon detecting a ventricular tachyarrhythmia during a normal, non-VAD mode of operation of the IMD. The co-implanted VAD may provide necessary hemodynamic support to the patient during a sustained ventricular tachyarrhythmia, reducing the urgency of an automatic cardioversion/defibrillation shock in some examples of a VAD mode of operation of the IMD.

In one example, the disclosure provides an IMD including a sensing circuit, a therapy delivery circuit, a telemetry circuit and a control circuit. The sensing circuit is configured to receive a cardiac electrical signal produced by a heart of a patient. The therapy delivery circuit is configured to generate an electrical stimulation therapy for delivery to the patient's heart. The telemetry circuit is configured to receive a command from another medical device indicating co-implantation of a VAD with the IMD in the patient. The control circuit is coupled to the sensing circuit, the therapy delivery circuit and the telemetry circuit and is configured to operate in a first mode including detecting a cardiac arrhythmia from the cardiac electrical signal and controlling the therapy delivery circuit to automatically deliver the electrical stimulation therapy in response to detecting the cardiac arrhythmia. The control circuit is further configured to switch from operating in the first mode to operating in a second mode in response to receiving the command. Switching to the second mode includes adjusting at least one control parameter used for controlling the electrical stimulation therapy.

In another example the disclosure provides a method performed by an IMD. The method includes operating the implantable medical device according to a first mode, receiving a command from another medical device indicating co-implantation of a ventricular assist device with the implantable medical device in the patient, and switching from the first mode of operating to a second mode of operating in response to receiving the command. The first mode includes detecting a cardiac arrhythmia from a cardiac electrical signal and automatically delivering an electrical stimulation therapy to a heart of a patient in response to detecting the cardiac arrhythmia. Switching from the first mode to the second mode comprises adjusting at least one control parameter used for controlling the electrical stimulation therapy.

In yet another example the disclosure provides a non-transitory, computer-readable storage medium storing a set of instructions which, when executed by a controller of an IMD, cause the IMD to receive a command from another medical device indicating co-implantation of a VAD with the IMD in a patient and switch from a first mode of operating to a second mode of operating in response to receiving the command. Operating according to the first mode includes detecting a cardiac arrhythmia from a cardiac electrical signal received by a sensing circuit of the IMD and controlling a therapy delivery circuit to automatically deliver an electrical stimulation therapy to a heart of the patient in response to detecting the cardiac arrhythmia. Switching from the first mode to the second mode includes adjusting at least one control parameter used for controlling the electrical stimulation therapy.

In yet another example, the disclosure provides an external programmer for programming an IMD. The programmer includes a display, a telemetry circuit configured for bidirectional communication with the IMD, and a processor configured to generate a user interface on the display. The user interface includes a VAD mode window for receiving user input to enable a VAD mode of operation of the IMD. The processor is further configured to control the telemetry circuit to transmit a VAD mode of operation command to the IMD in response to the user input enabling the VAD mode of operation.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
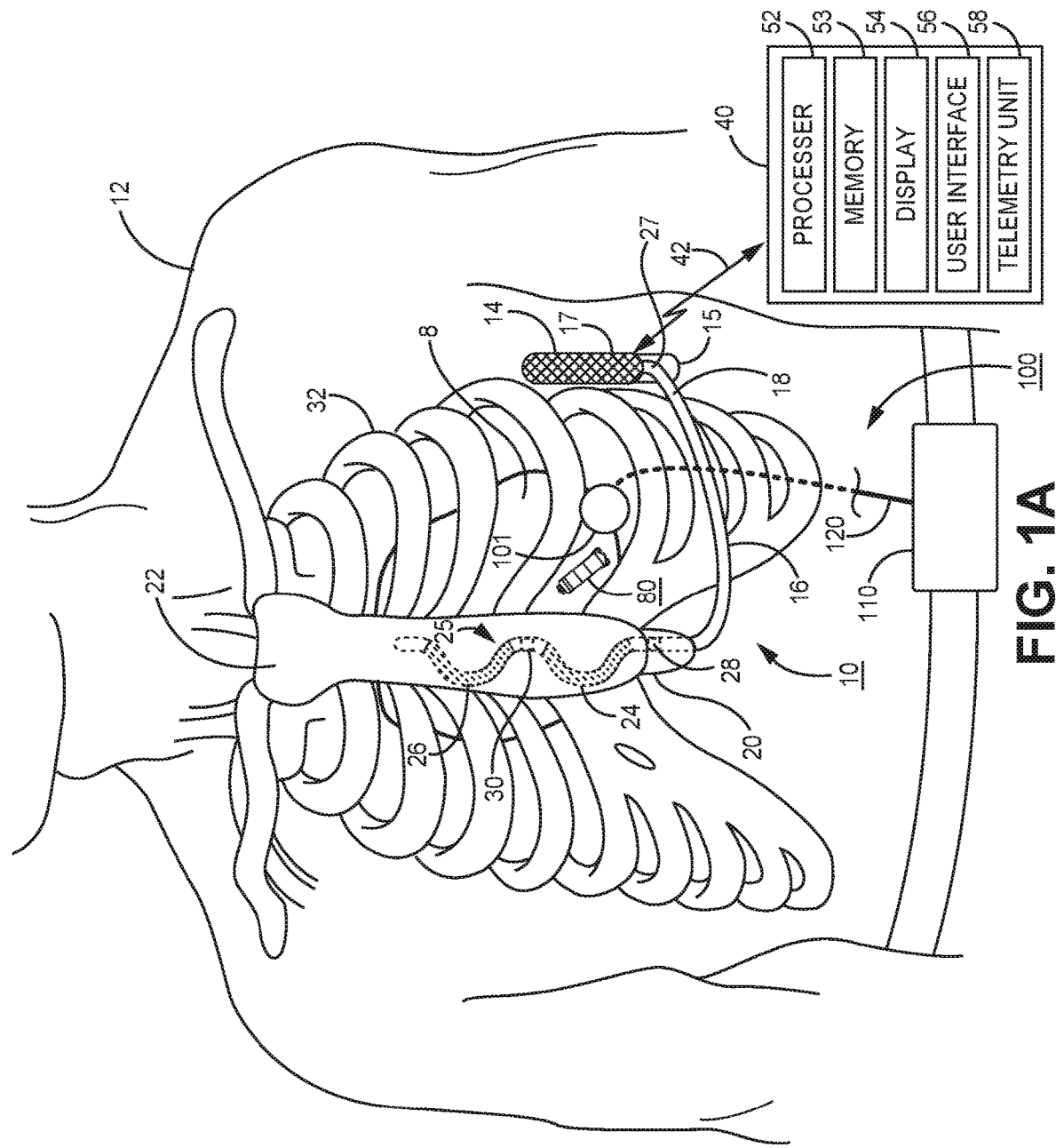
FIGS. 1A and 1B are conceptual diagrams of an IMD system including an ICD and a VAD coupled to a patient's heart according to one example.

In general, this disclosure describes a cardiac rhythm management IMD that is configurable to operate in an altered or adjusted operating mode when a VAD is co-implanted with the IMD. The VAD operating mode, also referred to herein as the "VAD mode," may include one or more adjusted therapy control parameters that are used to control delivery of cardiac electrical stimulation therapies delivered by the IMD. The VAD operating mode may include one or more adjusted monitoring and detection control parameters used by the IMD for detecting a patient condition, such as a cardiac arrhythmia. The VAD operating mode includes adjustments to IMD control parameters used for delivering therapy and/or detecting a cardiac arrhythmia, for example, that take into account the hemodynamic support provided by the VAD.

For example, an arrhythmia, which might normally cause the patient to become symptomatic or be life threatening in the absence of a VAD, may be tolerable for extended periods of time when the patient is supported by the VAD. As such, delivery of CV/DF shocks, which can cause pain and anxiety to a patient, or other arrhythmia therapies may be withheld or delayed when the patient has a VAD maintaining hemodynamic stability even in the presence of a sustained arrhythmia. Ventricular tachycardia (VT) or ventricular fibrillation (VF), which may be life threatening, may be treated by ATP or a CV/DF shock within seconds of being detected in a "non-VAD" operating mode of the IMD, when a VAD is not co-implanted in the patient. When a VAD is co-implanted in the patient, however, it is conceivable to withhold CV/DF shock therapy for terminating VT or VF for minutes, hours and perhaps even days since the VAD may maintain the patient in hemodynamically stable state. For example, in the presence of a VAD, an ICD may not need to respond as rapidly to a detected ventricular tachyarrhythmia as when the ICD is not co-implanted with a VAD. Patients with a VAD and an ICD could benefit from less urgent and/or less traumatic therapy delivered by the ICD. As such, tachyarrhythmia detection control parameters and/or therapy delivery control parameters as well as patient or clinician alert conditions, may be adjusted in the VAD operating mode compared to the normal operating mode of the IMD when a VAD is not co-implanted with the IMD.

The examples presented herein relate to a cardiac rhythm management IMD provided as an ICD capable of high voltage electrical stimulation therapies, e.g., CV/DF shocks. The ICD may be capable of delivering relatively lower voltage electrical stimulation therapies, such as cardiac pacing pulses for bradycardia pacing, post shock pacing, CRT and ATP. It is recognized that aspects of the techniques disclosed herein may be implemented in a pacemaker or other cardiac rhythm management IMD that may be configured to deliver cardiac pacing therapies without having high voltage CV/DF shock therapy capabilities. As such, while the examples that follow refer primarily to an ICD, practice of the techniques disclosed herein are not necessarily limited to use with an ICD that is co-implantable with a VAD and may be practiced in other IMDs configured to monitor the patient's cardiac rhythm and deliver cardiac electrical stimulation therapies.

For example, a pacemaker configured to deliver pacing therapy, which may include bradycardia pacing, post-shock pacing, CRT, and/or ATP as examples, may be configured to operate in a VAD operating mode as disclosed herein. A pacemaker operating in a VAD mode may be a leadless pacemaker implanted submuscularly, subcutaneously or wholly within a heart chamber (intracardiac) having electrodes mounted on the pacemaker housing. In other examples, a pacemaker operating in a VAD mode may be implanted in a subcutaneous or submuscular pocket and be coupled to extra-cardiovascular or transvenous cardiac leads extending from the pacemaker, in addition to or alternatively to one or more electrodes on the housing of the pacemaker.

Figure 1B:
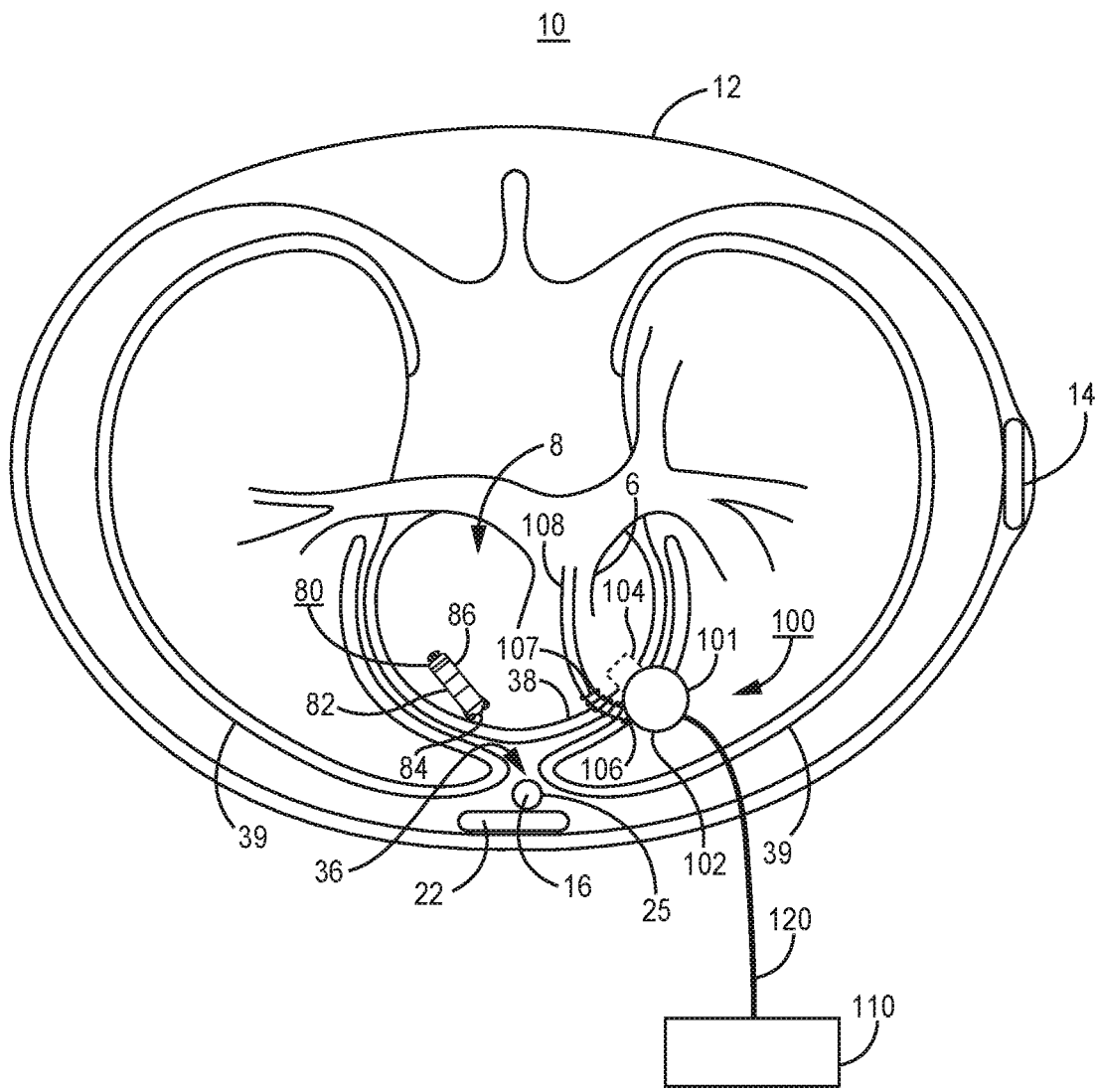

FIGS. 1A and 1B are conceptual diagrams of an IMD system 10 including an ICD 14 and a VAD 100 coupled to a patient's heart 8 according to one example. In some examples, an intracardiac pacemaker 80 may be included in IMD system 10 or may be co-implanted with VAD 100 without ICD14. FIG. 1A is a front view of IMD system 10 implanted within patient 12. FIG. 1B is a transverse view of IMD system 10 implanted within patient 12. ICD 14 is coupled to an extra-cardiovascular lead 16 carrying one or more electrodes for sensing cardiac electrical signals and for delivering cardiac electrical stimulation therapies. VAD 100 is shown as an implantable blood pump 101 which is fluidly coupled between a heart ventricle and an artery of patient 12. Blood pump 101 is electrically coupled to an external, wearable controller 110 via a percutaneous drive line 120 in the example shown. It is recognized, however, that a VAD that is co-implantable with ICD 14 may include a wholly implantable blood pump and controller or an external blood pump and controller in other examples. In some examples, the blood pump and controller may be integrated. While a single VAD is shown in FIG. 1, it is recognized that multiple VADs may be co-implanted with ICD 14 and/or pacemaker 80 (or other cardiac rhythm management device), for instance to provide bi-ventricular assist using two blood pumps.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 is connected to an extra-cardiovascular electrical stimulation and sensing lead 16. ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, controlling and delivering electrical stimulation pulses to treat an abnormal heart rhythm, and for communicating with an external programmer 40. In some examples, ICD 14 may be configured to communicate with VAD 100.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In other examples, lead 16 may include only a single defibrillation electrode or more than two defibrillation electrodes.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage CV/DF shock therapy applications. For example, electrodes 24 and 26 may be used in a sensing vector used to sense cardiac electrical signals and detect and discriminate cardiac arrhythmias.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage cardioversion defibrillation shocks. In some instances, electrodes 28 and 30 may provide only pacing functionality, only sensing functionality or both.

ICD 14 may obtain cardiac electrical signals corresponding to electrical activity of heart 8 via one or more sensing vectors that include combinations of electrodes 24, 26, 28 and/or 30. In some examples, housing 15 of ICD 14 is used in combination with one or more of electrodes 24, 26, 28 and/or 30 in a sensing electrode vector. In one example, a sensing vector includes electrodes 28 and 30. In another example, a sensing vector includes defibrillation electrode 24 and housing 15. These examples are illustrative in nature and not intended as limiting. Various sensing electrode vectors utilizing combinations of electrodes 24, 26, 28, and 30 and housing 15 may be used for acquiring one or more cardiac electrical signals received by sensing circuitry included in ICD 14.

In the example illustrated in FIGS. 1A and 1B, electrode 28 is located proximal to defibrillation electrode 24, and electrode 30 is located between defibrillation electrodes 24 and 26. Lead 16 may include none, one, two or more pace/sense electrodes, which, when present, may be carried at other locations along lead body 18 than the particular locations shown. Electrodes 28 and 30 are illustrated as ring electrodes but may comprise any of a number of different types of electrodes, including ring electrodes, short coil electrodes, hemispherical electrodes, directional electrodes, segmented electrodes, or the like.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18 are each electrically coupled with respective defibrillation electrodes 24 and 26 and pace/sense electrodes 28 and 30, which may be separate respective insulated conductors within the lead body 18. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No.

2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves. Various example configurations of extra-cardiovascular leads and electrodes and dimensions that may be implemented in conjunction with the therapy management techniques disclosed herein are described in pending U.S. Publication No. 2015/0306375 (Marshall, et al.) and U.S. Pat. No. 9,855,414 (Marshall, et al.), both of which are incorporated herein by reference in their entirety.

Lead 16 is shown to extend medially from the connector assembly 27 of ICD 14, subcutaneously or submuscularly over the ribcage 32 toward a center of the torso of patient 12, e.g., toward xiphoid process 20. At a location near xiphoid process 20, lead 16 bends or turns and extends superiorly and substernally under the ribcage and/or sternum, substantially parallel to sternum 22. Anterior mediastinum 36 (see FIG. 1B) may be viewed as being bounded laterally by pleurae 39, posteriorly by pericardium 38, and anteriorly by sternum 22 (see FIG. 1B). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 1A and 1B, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8. In other embodiments, the distal portion 25 of lead 16 may be implanted in other extra-cardiovascular locations, such as subcutaneous, submuscular or other extra-thoracic locations.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. The path of extra-cardiovascular lead 16 may depend on the location of ICD 14, the arrangement and position of electrodes carried by the lead body 18, the location of VAD 100, and/or other factors.

ICD 14 analyzes the cardiac electrical signals received from one or more sensing electrode vectors to monitor for abnormal rhythms, such as bradycardia, supraventricular tachycardia (SVT), VT and VF. ICD 14 may analyze the heart rate and morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated herein by reference in its entirety. A variety of arrhythmia detection algorithms may be implemented in ICD 14 for detecting an abnormal heart rhythm.

ICD 14 may generate and deliver electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver ATP in response to VT detection, and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

An external programmer 40 is shown in telemetric communication with ICD 14 by a communication link 42. External programmer 40 may include a processor 52, memory 53, display unit 54, user interface 56 and telemetry unit 58. Processor 52 controls external programmer operations and processes data and signals received from ICD 14. Display unit 54, which may include a graphical user interface, displays data, programmable selections and settings and other information to a user for reviewing ICD operation, programming operating parameters and modes, and reviewing cardiac electrical signals retrieved from ICD 14. For example, a user may select the VAD operating mode using a graphical user interface of display unit 54 and program any user-programmable settings of the VAD operating mode, as further described below in conjunction with FIG. 8.

User interface 56 may include a mouse, touch screen, key pad or the like to enable a user to interact with external programmer 40 to initiate a telemetry session with ICD 14 for retrieving data from and/or transmitting data to ICD 14. Telemetry unit 58 includes a transceiver and antenna configured for bidirectional communication with a telemetry circuit included in ICD 14 and is configured to operate in conjunction with processor 52 for sending and receiving data relating to ICD functions via communication link 42 Communication link 42 may be established between ICD 14 and external programmer 40 using a radio frequency (RF) link such as BLUETOOTH®, Wi-Fi, or Medical Implant Communication Service (MICS) or other RF or communication frequency bandwidth.

External programmer 40 may be embodied as a programmer used in a hospital, clinic or physician's office to retrieve data from ICD 14 and to program operating parameters and algorithms in ICD 14 for controlling ICD functions. External programmer 40 may alternatively be embodied as a home monitor or hand held device. External programmer 40 may be used to program cardiac event sensing parameters (e.g., R-wave sensing parameters), cardiac rhythm detection parameters (e.g. number of VT or VF intervals required to detect a VT or VF episode, respectively), and therapy control parameters used by ICD 14. Data stored or acquired by ICD 14, including physiological signals or associated data derived therefrom, results of device diagnostics, and histories of detected rhythm episodes and delivered therapies, may be retrieved from ICD 14 by external programmer 40 following an interrogation command.

External programmer 40 may be used to enable the VAD mode of ICD 14. A clinician or other authorized user may enable the VAD mode. An authorized user may enable the VAD mode by selecting a VAD mode "button" or field on a display of external programmer 40. The user may be required or prompted to enter one or more authentication entries in order to confirm co-implantation of a VAD and prevent inappropriate or inadvertent programming of ICD 14 in the VAD mode when a VAD is not present. For instance, entry of the VAD model and/or serial number or other patient-specific information confirming and authenticating co-implantation of the VAD 100 with ICD 14 may be required. In some examples, controller 110 of VAD 100 and ICD 14 may be configured to communicate via wireless telemetry in which case VAD 100 may transmit a signal to ICD 14 confirming co-implantation and validating the VAD mode of operation of ICD 14.

The VAD mode may be enabled by selection of a single button or field on external programmer display 54, which then causes transmission of a VAD mode command to ICD 14. In other examples, VAD 100 may transmit a communication signal notifying ICD 14 of the presence of the co-implanted VAD 100. ICD 14 may respond to receipt of the VAD mode command by automatically adjusting arrhythmia detection parameters, therapy parameters, monitoring parameters, and/or alert parameters according to default VAD mode operating control parameters. In other examples, additional user programmable settings of the VAD mode may be selected by a user interacting with external programmer 40 and programmed in ICD 14 by uplink telemetry to ICD 14.

In the example shown, VAD 100 includes an implantable blood pump 101 and external wearable controller 110. VAD 100 may take the form of any one of a variety of blood pumps such as an impeller-driven or pneumatic-driven pump providing pulsatile or non-pulsatile flow, an extracorporeal membrane oxygenation (ECMO) system, an intra-aortic balloon pump, or other mechanical circulatory support device configured to assist the mechanical pumping function of the heart. In the example of FIG. 1, blood pump 101 may be a centrifugal, rotary blood pump having a pump housing 102 enclosing an interior pump chamber and rotary impeller. Blood pump 101 is shown coupled between the patient's heart 8 and an artery, as best seen in FIG. 1B. For example, blood pump 101 may be coupled between the left ventricle (LV) and the ascending aorta 6 to pump blood in parallel with the LV into the arterial system. The interior pump chamber is in fluid communication with an inflow cannula 104 that may be inserted into the LV, e.g. via a sewing ring, for receiving blood from the patient's heart 8. At least a portion of the exterior circumferential surface of inflow cannula 104 may be sintered to promote tissue adhesions between the ventricular myocardium and inflow cannula 104. Pump housing 102 may have a relatively low profile, e.g., an overall height of 30 mm or less, so that pump housing 102 may be implanted within the pericardial space in some examples. To accommodate implantation within the pericardial space, inflow cannula 104 may be relatively short, e.g., 60 mm or less. In other examples, blood pump 101 may be implanted intrathoracically but outside the pericardial space or may be an external, wearable blood pump.

The interior of the pump housing 102 is also in fluid communication with a flow outlet 106 that is coupled to an outflow vascular graft 108. Graft 108 is anastomosed to the ascending aorta 6 (or other artery) to direct the pump outflow into the patient's arterial system. In some examples, graft 108 may be an 8 to 12 mm diameter graft fabricated from a polyester material. Graft 108 may include a strain relief member 107 to prevent kinking of vascular graft 108. Strain relief member 107 may extend from flow outlet 106 exteriorly along at least a portion of the length of vascular graft 108. Strain relief member 107 may be formed of a coiled metal or plastic material that provides flexibility of the proximal portion of vascular graft 108 but resists kinking.

Controller 110 is shown as a wearable device that includes one or more rechargeable batteries and/or power supply connections (e.g., an AC power supply connection) to provide power to the controller 110. In other examples, controller 110 may be implantable and may include a transcutaneously rechargeable power source. Blood pump 101 may include motor stators that receive a drive current from controller 110 via percutaneous drive line 120. VAD 100 may be a continuous flow pump and may have a constant or variable speed, such as the pump generally disclosed in U.S. Pat. No. 9,433,714 (Voskoboynikov et al.), incorporated herein by reference in its entirety.

FIGS. 1A and 1B are illustrative in nature and should not be considered limiting of the practice of the techniques disclosed herein. For example, the implant locations of ICD 14, lead 16 and blood pump 101 may be different than the particular locations shown in FIGS. 1A and 1B. Furthermore, other ICD and lead systems and/or other VAD systems may be substituted for the example ICD 14 and VAD 100 shown in system 10 and configured to perform the techniques disclosed herein. For example, VAD 100 may be a wholly implantable device.

Intracardiac pacemaker 80 may be co-implanted with VAD 100 in some examples. Intracardiac pacemaker 80 includes a housing 82 enclosing internal circuitry and components for receiving a cardiac electrical signal produced by heart 8 via electrodes 84 and 86 on housing 82. Housing 82 encloses a pulse generator for generating cardiac pacing pulses delivered to heart 8 via electrodes 84 and 86. Pacemaker 80 may be configured to deliver bradycardia pacing pulses, ATP, post-shock pacing pulses, CRT, atrial synchronous ventricular pacing, or other pacing therapies. Pacemaker 80 may be configured to switch to a VAD operating mode in response to a command received from external programmer 40 or a communication signal from VAD 100 or ICD 14 (if present). Pacemaker 80 may be configured to switch to the VAD mode by adjusting at least one control parameter that is used to control cardiac pacing pulse delivery during the VAD mode.

Pacemaker 80 is shown implanted in the right ventricle of heart 8 in FIGS. 1A and 1B with VAD 100 coupled to the left ventricle. In other examples, intra-cardiac pacemaker 80 may be implanted in a different heart chamber, e.g., the left ventricle, particularly when VAD 100 is coupled to the right ventricle instead of the left ventricle. As described below, switching to the VAD mode by a pacemaker such as pacemaker 80 may include increasing the use of ATP therapy in response to detecting a ventricular tachyarrhythmia and/or enabling, disabling or otherwise adjusting ventricular pacing. Pacemaker 80 may generally correspond to the intracardiac pacemaker disclosed in U.S. Pat. No. 9,808,637 (Sharma, et al.), incorporated herein by reference in its entirety.

Figure 2:
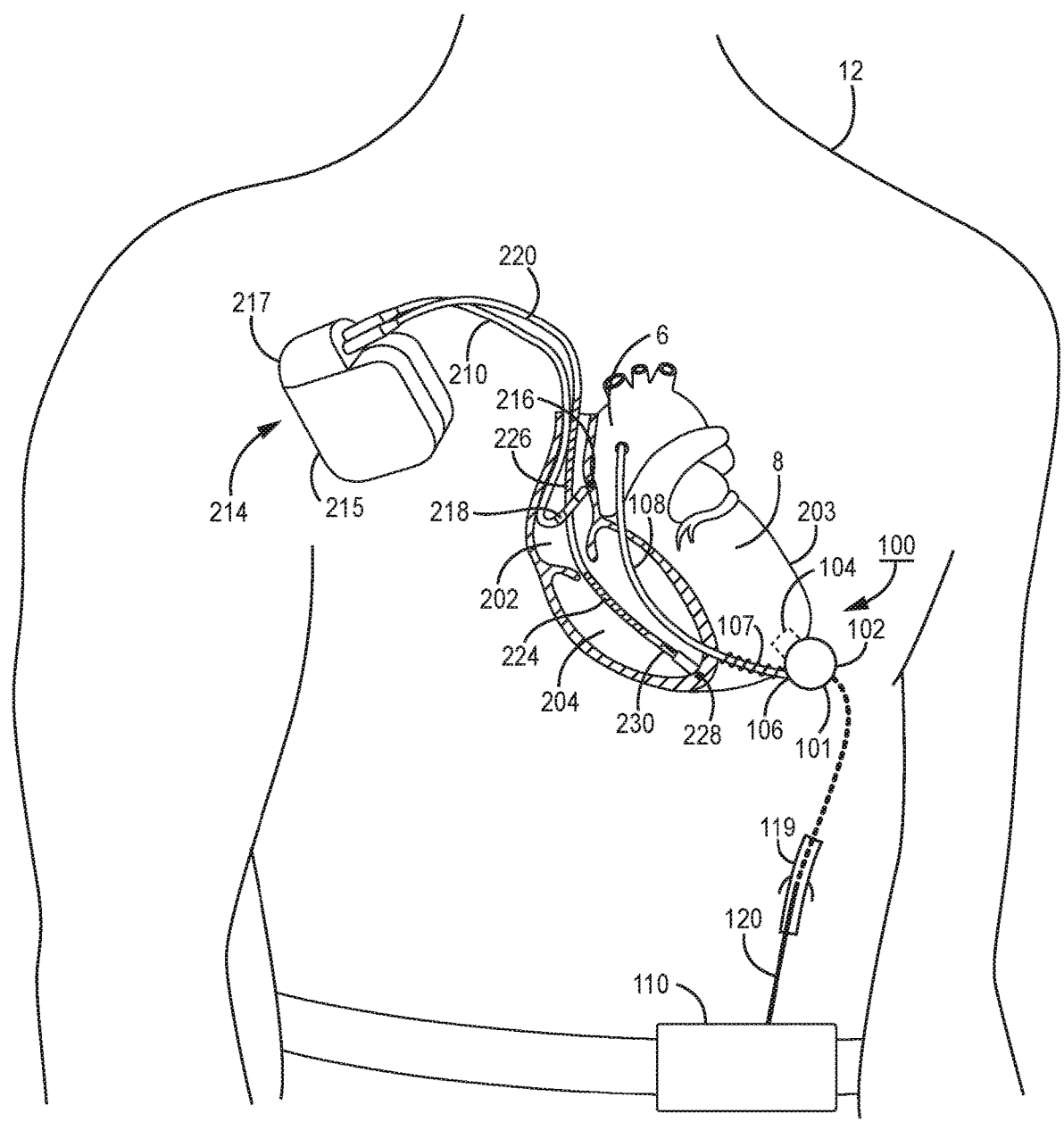
FIG. 2 is a conceptual diagram of a patient implanted with an IMD system including an ICD and VAD according to another example.

FIG. 2 is a conceptual diagram of patient 12 implanted with an IMD system 200 including an ICD 214 and VAD 100 according to another example. In this example, ICD 214 is coupled to transvenous leads carrying electrodes for sensing cardiac electrical signals and delivering electrical stimulation pulses to heart 8 for cardiac rhythm management, such as bradycardia pacing, post-shock pacing, ATP, CRT and/or CV/DF shocks as examples. ICD 214 is shown implanted in a right pectoral position in FIG. 2; however it is recognized that ICD 214 may be implanted in a left pectoral position, particularly when ICD 214 includes cardioversion and defibrillation capabilities using housing 215 as an electrode.

ICD 214 is illustrated as a dual chamber device for sensing and therapy delivery in an atrial chamber 202 and a ventricular chamber 204 of heart 8. As such, ICD 214 includes connector assembly 217 having two connector bores for receiving proximal connectors of a right atrial (RA) lead 210 and a right ventricular (RV) lead 220. In other examples ICD 214 may be a single chamber device, e.g., connectable only to RV lead 220, or a multi-chamber device including a third connector bore, e.g., for receiving a coronary sinus lead to enable ICD 214 to sense left ventricular signals and deliver electrical stimulation pulses to the LV 203.

RA lead 210 may carry a distal tip electrode 216 and ring electrode 218 spaced proximal from the tip electrode 216 for delivering pacing pulses to the RA 202 and obtaining atrial electrical signals for producing an atrial intra-cardiac electrogram (EGM) signal by ICD 214. RV lead 220 may carry pacing and sensing electrodes 228 and 230 for delivering RV pacing pulses to the RV 204 and obtaining ventricular electrical signals for producing an RV EGM signal by ICD 214. RV lead 220 may also carry RV defibrillation electrode 224 and a superior vena cava (SVC) defibrillation electrode 226. Defibrillation electrodes 224 and 226 are shown as coil electrodes spaced apart proximally from the distal pacing and sensing electrodes 228 and 230.

ICD housing 215 encloses circuitry, as further described below, configured to detect arrhythmias and provide electrical stimulation therapy, such as bradycardia pacing, post-shock pacing, ATP, CRT and/or CV/DF shock therapy, using the electrodes 216, 218, 224, 226, 228 and 230 of transvenous leads 210 and 220. ICD 214 is configured to operate in a VAD mode for the purposes of managing arrhythmia monitoring and cardiac electrical stimulation therapy delivery when patient 12 has the hemodynamic support provided by VAD 100.

As described in conjunction with FIGS. 1A and 1B, VAD 100 includes blood pump 101 having a pump housing 102 that encloses an interior pump chamber for receiving blood through inflow cannula 104 from the left ventricle 203 of heart 8. Pump housing 102 may enclose a rotary impeller motor that drives blood through the interior pump chamber and out of flow outlet 106, through vascular graft 108, and into the ascending aorta 6. The percutaneous drive line 120 provides power and control signals from external controller 110, wearable by patient 12, to electromagnetic stators of the motor. Drive line 120 may include an exterior, circumferential sheath 119 of woven polyester or other biocompatible woven or porous material to promote tissue in-growth at the skin exit site of percutaneous drive line 120.

Figure 3:
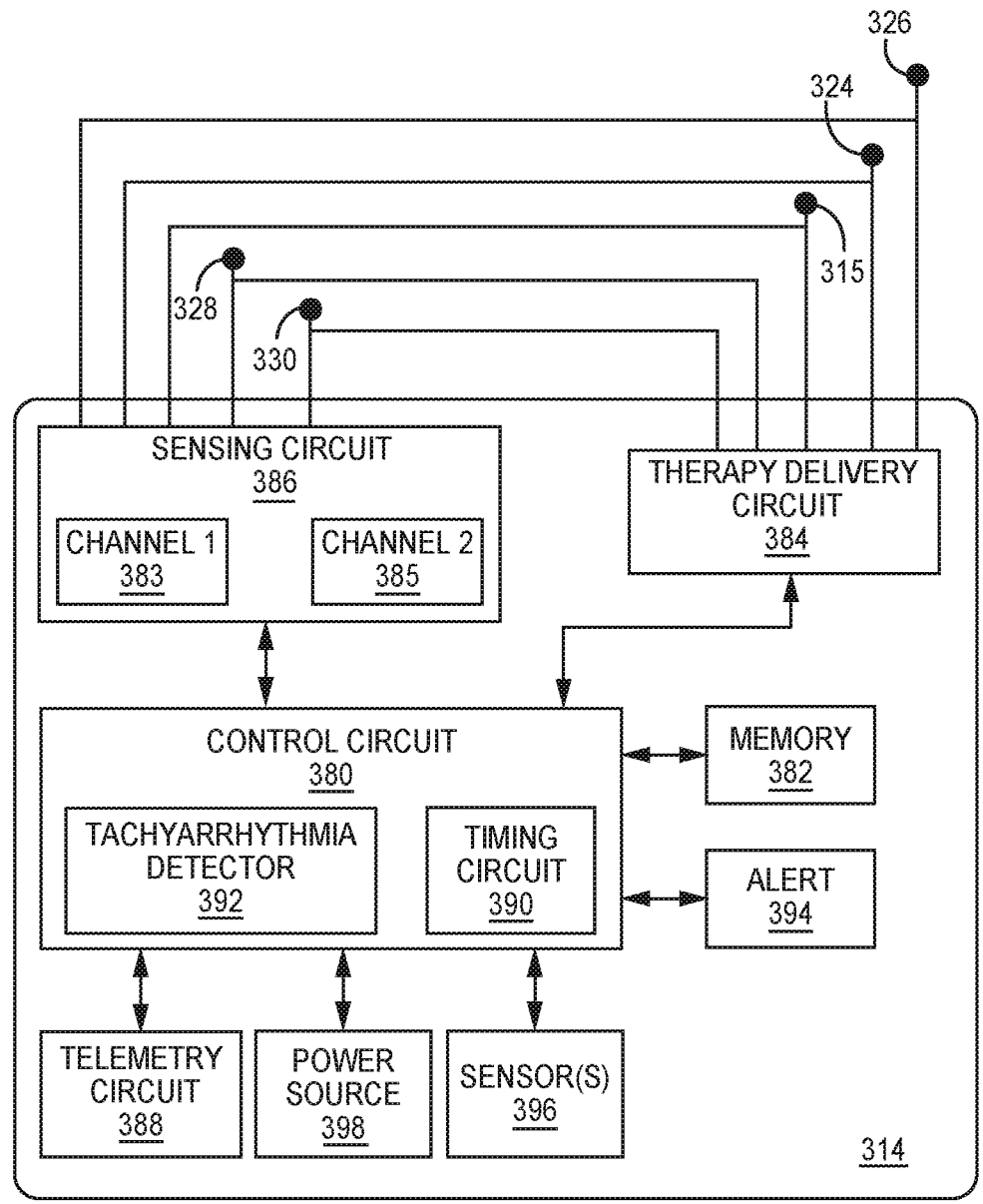
FIG. 3 is a schematic diagram of an ICD that may be co-implanted with a VAD and configured to operate in a VAD mode according to one example.

FIG. 3 is a schematic diagram of an ICD 314 that may be co-implanted with VAD 100 and configured to operate in a VAD mode. The circuitry shown and described in FIG. 3 may correspond to circuitry included in ICD 14 of FIG. 1A or in ICD 214 of FIG. 2. The electronic circuitry enclosed within housing 315 (shown schematically as an electrode in FIG. 3) includes software, firmware and hardware that cooperatively monitor cardiac electrical signals produced by the patient's heart, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and determine when ATP and/or CV/DF shocks are required. ICD 314 is coupled to one or more leads carrying electrodes 324, 326, 328, and 330, e.g., an extra-cardiovascular lead such as lead 16 shown in FIG. 1A or transvenous leads such as leads 210 and 220 shown in FIG. 2, for delivering electrical stimulation pulses to the patient's heart and for sensing cardiac electrical signals.

ICD 314 includes a control circuit 380, memory 382, therapy delivery circuit 384, sensing circuit 386, and telemetry circuit 388. ICD 314 may include a patient alert 394 and/or one or more physiological sensors 396 other than the cardiac electrical signal sensing electrodes coupled to sensing circuit 386 and therapy delivery circuit 384. A power source 398 provides power to the circuitry of ICD 314, including each of circuits 380, 382, 384, 386, 388, 394 and 396 as needed. Power source 398 may include one or more energy storage devices, such as one or more rechargeable or non-rechargeable batteries. The connections between power source 398 and each of the other components 380, 382, 384, 386, 388, 394 and 396 are to be understood from the general block diagram of FIG. 3, but are not shown for the sake of clarity. For example, power source 398 may be coupled to one or more charging circuits included in therapy delivery circuit 384 for charging holding capacitors included in therapy delivery circuit 384 that are discharged at appropriate times under the control of control circuit 380 for producing electrical pulses according to a therapy protocol, such as for bradycardia pacing, CRT, post-shock pacing, ATP and/or CV/DF shock pulses. Power source 398 may also be coupled to components of sensing circuit 386, such as sense amplifiers, analog-to-digital converters, switching circuitry, etc., telemetry circuit 388, alert 394, sensors 396 and memory 382 to provide power as needed.

The functional blocks shown in FIG. 3 represent functionality included in an ICD configured to sense cardiac electrical signals and deliver cardiac electrical stimulation therapy and may include any discrete and/or integrated electronic circuit components that implement analog and/or digital circuits capable of producing the functions attributed to an ICD herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern IMD system, given the disclosure herein, is within the abilities of one of skill in the art.

Memory 382 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 382 may include non-transitory computer readable media storing instructions that, when executed by one or more processing circuits, cause control circuit 380 and/or other ICD components to perform various functions attributed to ICD 314 or those ICD components. The non-transitory computer-readable media storing the instructions may include any of the media listed above.

The functions attributed to ICD 314 herein may be embodied as one or more integrated circuits. Depiction of different features as circuits is intended to highlight different functional aspects and does not necessarily imply that such circuits must be realized by separate hardware or software components. Rather, functionality associated with one or more circuits may be performed by separate hardware, firmware or software components, or integrated within common hardware, firmware or software components. For example, cardiac event sensing and tachyarrhythmia detection operations may be performed cooperatively by sensing circuit 386 and control circuit 380 and may include operations implemented in a processor or other signal processing circuitry included in control circuit 380 executing instructions stored in memory 382 that produce control signals such as blanking and timing intervals and sensing threshold amplitude signals sent from control circuit 380 to sensing circuit 386.

Control circuit 380 controls ICD 314 to operate in a normal, non-VAD operating mode when ICD 314 is not co-implanted with VAD 100. The non-VAD mode may be the default operating mode that is enabled in ICD 314 at the time of device manufacture or otherwise programmed into ICD 314 when implanted or at a follow-up appointment. When ICD 314 is co-implanted with VAD 100, ICD 314 transitions to operate in the VAD mode. In the VAD mode, one or more therapies delivered by ICD 314 and considered urgent during the non-VAD mode may be considered less urgent and be delayed or withheld. Control circuit 380 communicates, e.g., via a data bus, with therapy delivery circuit 384 and sensing circuit 386. Therapy delivery circuit 384 and sensing circuit 386 are electrically coupled to electrodes 324, 326, 328, 330 and the housing 315, which may function as a common or ground electrode or as an active can electrode for delivering CV/DF shock pulses or cardiac pacing pulses. In the example ICD 214 of FIG. 2, additional atrial electrodes 216 and 218 carried by a transvenous atrial lead 210 may be coupled to sensing circuit 386 and therapy delivery circuit 384.

Sensing circuit 386 may be selectively coupled to electrodes 328, 330 and/or housing 315 in order to monitor electrical activity of the patient's heart. Sensing circuit 386 may additionally be selectively coupled to defibrillation electrodes 324 and/or 326 for use in a sensing electrode vector together or in combination with one or more of electrodes 328, 330 and/or housing 315. Sensing circuit 386 may be enabled to selectively receive cardiac electrical signals from at least two sensing electrode vectors from the available electrodes 324, 326, 328, 330, and housing 315. Two cardiac electrical signals from two different sensing electrode vectors may be received simultaneously by sensing circuit 386. The two sensing electrode vectors may include two different ventricular sensing electrode vectors each coupled to a respective sensing channel 383 and 385. In other examples, when an atrial sensing electrode vector is available, e.g., when RA lead 210 is present carrying atrial pacing and sensing electrodes 216 and 218 (as shown in FIG. 2), one sensing channel 383 may be an atrial sensing channel coupled to atrial sensing electrodes and one sensing channel 385 may be a ventricular sensing channel coupled to ventricular sensing electrodes.

Sensing circuit 386 may monitor one or both of the cardiac electrical signals at a time for sensing cardiac electrical events, e.g., P-waves attendant to the depolarization of the atrial myocardium and/or R-waves attendant to the depolarization of the ventricular myocardium, and providing digitized cardiac signal waveforms for analysis by control circuit 380. For example, sensing circuit 386 may include switching circuitry for selecting which of electrodes 324, 326, 328, 330, and housing 315 are coupled to a first sensing channel 383 and which are coupled to a second sensing channel 385 of sensing circuit 386. Switching circuitry may include a switch array, switch matrix, multiplexer, or any other type of switching device suitable to selectively couple components of sensing circuit 386 to selected electrodes.

Each sensing channel 383 and 385 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 386 may include one or more sense amplifiers, filters, rectifiers, threshold detectors, comparators, analog-to-digital converters (ADCs), timers or other analog or digital components. A cardiac event sensing threshold may be automatically adjusted by sensing circuit 386 under the control of control circuit 380, based on timing intervals and sensing threshold values determined by control circuit 380, stored in memory 382, and/or controlled by hardware, firmware and/or software of control circuit 380 and/or sensing circuit 386.

Upon detecting a cardiac electrical signal (e.g., an R-wave or P-wave) based on a sensing threshold crossing, sensing circuit 386 may produce a sensed event signal, such as an R-wave sensed event signal, that is passed to control circuit 380. The R-wave sensed event signals are also used by control circuit 380 for determining ventricular event intervals, referred to as "RR intervals" or "RRIs" for detecting tachyarrhythmia and determining a need for therapy. A ventricular event interval or RRI is the time interval between two consecutively sensed R-waves and may be determined between two consecutive R-wave sensed event signals received from sensing circuit 386. For example, control circuit 380 may include a timing circuit 390 for determining RRIs between consecutive R-wave sensed event signals received from sensing circuit 386 and for controlling various timers and/or counters used to control the timing of therapy delivery by therapy delivery circuit 384. Timing circuit 390 may additionally set time windows such as morphology template windows, morphology analysis windows or perform other timing related functions of ICD 314 including synchronizing CV/DF shocks or other therapies delivered by therapy delivery circuit 384 with sensed cardiac events. In the VAD mode, shock therapy may be withheld or delayed. Timing circuit 390 may track the duration of a VT or VF episode for use in determining VT or VF burden and/or a maximum VT or VF episode time before delivering a therapy or generating a physician and/or patient alert.

Tachyarrhythmia detector 392 is configured to analyze signals received from sensing circuit 386 for detecting tachyarrhythmia episodes. Tachyarrhythmia detector 392 may be implemented in control circuit 380 as software, hardware and/or firmware that processes and analyzes signals received from sensing circuit 386 for detecting VT and/or VF. In some examples, tachyarrhythmia detector 392 may include comparators and counters for counting RRIs determined by timing circuit 390 that fall into various rate detection zones for determining a ventricular rate or performing other rate- or interval-based assessments for detecting and discriminating VT and VF. For example, tachyarrhythmia detector 392 may compare the RRIs determined by timing circuit 390 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 392.

When a VT or VF interval counter reaches a threshold count value, referred to as "number of intervals to detect" or "NID," a ventricular tachyarrhythmia may be detected by control circuit 380. Tachyarrhythmia detector 392 may be configured to perform other signal analysis for determining if other detection criteria are satisfied before detecting VT or VF when an NID is reached. For example, cardiac signal analysis may be performed to determine if R-wave morphology criteria, onset criteria, and noise and oversensing rejection criteria are satisfied in order to determine if the VT/VF detection should be made or withheld. As disclosed herein, tachyarrhythmia detector 392 may use different detection parameter values, e.g., a higher NID, when operating in the VAD mode compared to a normal, non-VAD operating mode. Control circuit 380 may withhold or delay a VT or VF detection when ICD 314 is operating in the VAD mode. In other examples, control circuit 380 may withhold or delay a therapy delivered by therapy delivery circuit 384 when tachyarrhythmia detector 392 detects VT or VF, but ICD 314 is operating in the VAD mode. In this case, VT and VF detection criteria, such as the NID, may or may not remain the same during the VAD mode as in the non-VAD mode.

To support additional cardiac signal analyses performed by tachyarrhythmia detector 392, sensing circuit 386 may pass a digitized cardiac electrical signal to control circuit 380. A cardiac electrical signal from the selected sensing channel, e.g., from first sensing channel 383 and/or the second sensing channel 385, may be passed through a filter and amplifier, provided to a multiplexer and thereafter converted to multi-bit digital signals by an analog-to-digital converter, all included in sensing circuit 386, for storage in memory 382. Additional signal analyses may include morphological analysis of pre-determined time segments of the cardiac electrical signals or QRS waveforms. Morphological analysis may include waveform template matching, e.g., using wavelet transform coefficients for classifying heart beats. In some tachyarrhythmia detection schemes, one or more time segments of a received cardiac electrical signal, for example two or more three 3-second cardiac signal segments, may be analyzed for determining whether the cardiac signal segment should be classified as a tachyarrhythmia that is treatable by a CV/DF shock.

In some examples, additional analysis of cardiac electrical signals received from sensing circuit 386 may be performed by control circuit 380 for monitoring the patient's cardiac status during the VAD mode. For example, during a sustained ventricular tachyarrhythmia, control circuit 380 may be configured to monitor for a deterioration or worsening in the cardiac rhythm or monitor for myocardial ischemia based on changes in the T-wave of a ventricular electrical signal, such as changes in T-wave amplitude, polarity, Q-T interval, or the like. Acceleration in a ventricular tachyarrhythmia, evidence of myocardial ischemia, or other worsening cardiac condition indicated by the cardiac electrical signal analysis may warrant delivery of a delayed or withheld therapy in the VAD mode and/or generating a patient and/or physician alert.

Therapy delivery circuit 384 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 384 according to control signals received from control circuit 380. Timing circuit 390 of control circuit 380 may include various timers or counters that control when ATP or other cardiac pacing pulses are delivered. For example, timing circuit 390 may include programmable digital counters set by a microprocessor of the control circuit 380 for controlling the basic pacing time intervals associated with various pacing modes or ATP sequences delivered by ICD 314. The microprocessor of control circuit 380 may also set the amplitude, pulse width, polarity or other characteristics of the cardiac pacing pulses, which may be based on programmed values stored in memory 382.

In response to detecting VT or VF during the normal non-VAD mode, control circuit 380 may control therapy delivery circuit 384 to deliver therapies such as ATP and/or CV/DF therapy. The therapy response to a VT and/or VF detection in the VAD mode may be modified from the therapy response provided in the non-VAD mode as described herein. Therapy can be delivered by initiating charging of high voltage capacitors via a charging circuit, both included in therapy delivery circuit 384. Charging is controlled by control circuit 380, which monitors the voltage on the high voltage capacitors passed to control circuit 380 via a charging control line. When the voltage reaches a predetermined value set by control circuit 380, a logic signal is generated on a capacitor full line and passed to therapy delivery circuit 384, terminating charging. A CV/DF pulse is delivered to the heart under the control of the timing circuit 390 by an output circuit of therapy delivery circuit 384 via a control bus. The output circuit may include an output capacitor through which the charged high voltage capacitor is discharged via switching circuitry, e.g., an H-bridge, which determines the electrodes used for delivering the cardioversion or defibrillation pulse and the pulse wave shape. In some examples, the high voltage therapy circuit configured to deliver CV/DF shock pulses can be controlled by control circuit 380 to deliver pacing pulses, e.g., for delivering ATP or post shock pacing pulses. In other examples, therapy delivery circuit 384 may include a low voltage therapy circuit for generating and delivering relatively lower voltage pacing pulses for a variety of pacing needs.

Control parameters utilized by control circuit 380 for detecting cardiac arrhythmias and controlling therapy delivery may be programmed into memory 382 via telemetry circuit 388. Telemetry circuit 388 may include a transceiver and antenna for communicating with external device 40 (shown in FIG. 1A) using RF communication as described above. Under the control of control circuit 380, telemetry circuit 388 may receive downlink telemetry from and send uplink telemetry to external device 40. ICD 314 may receive a VAD mode command from external programmer 40 via telemetry circuit 388.

Telemetry circuit 388 may be used to transmit and receive communication signals to/from another medical device implanted in patient 12, such as VAD 100. VAD 100 and ICD 314 may be configured to communicate via wireless RF communication though other communication techniques may be used. ICD 314 may be configured to confirm the presence of VAD 100 via wireless communication, e.g., with external controller 110, before enabling the VAD mode of operation of ICD 314. ICD 314 may be configured to transmit a VT or VF detection signal to VAD controller 110. VAD 100 may adjust a drive signal to pump 101 to change the pump speed and flow rate in response to the VT or VF detection. In some examples, the pump speed may be decreased to prevent a suction event. In other examples, the pump speed may be increased to increase the flow rate to provide increased hemodynamic support.

In some examples, ICD 314 may include an alert circuit 394. Alert circuit 394 may be configured to generate an audible alert signal under the control of control circuit 380 when an alert condition is detected or alert criteria are met. As described below, during the VAD mode of operation, ICD 314 may detect VT or VF but withhold or delay a CV/DF shock, limit the number of shock attempts made to terminate the VT or VF, and/or increase the use of ATP in terminating the detected VT or VF episode compared to the normal, non-VAD operating mode. Control circuit 380 may be configured to control alert circuit 394 to generate an alert to notify the patient and/or caregiver of the detected tachyarrhythmia, notify the patient of a scheduled but delayed shock therapy, notify the patient to manually initiate a shock therapy, and/or contact his/her clinician or seek medical attention. In other examples, control circuit 380 may be configured to generate an alert by controlling telemetry circuit 388 to transmit an alert signal to an external device, e.g., external programmer 40. The external programmer 40 may be a home monitoring device coupled to a patient care database and network so that the patient's clinician is notified of the alert and may manually schedule a shock therapy from a remote location via the patient care network and/or schedule a patient follow up visit as needed.

In some examples, ICD 314 includes one or more physiological sensors 396 for monitoring respective physiological signals other than the cardiac electrical signal(s) received by sensing circuit 386. As examples, sensor(s) 396 may include an accelerometer for monitoring patient activity and/or posture; a temperature sensor for monitoring patient body temperature; an acoustical sensor for monitoring heart sounds or respiration; an impedance sensor from monitoring thoracic impedance; an oxygen sensor, e.g., an optical sensor, for monitoring tissue or blood oxygen saturation; and/or a pressure sensor for monitoring blood pressure. In switching from a normal, non-VAD mode of operation to the VAD mode of operation, ICD 314 may be configured to enable or adjust monitoring of one or more physiological signals received from sensors 396 for detecting a change in physiological condition of the patient during the VAD mode. Detection of a change in a physiological condition may cause control circuit 380 to control alert 394 and/or telemetry circuit 388 to generate/transmit an alert signal and/or control therapy delivery circuit to schedule a withheld or delayed therapy.

Figure 4:
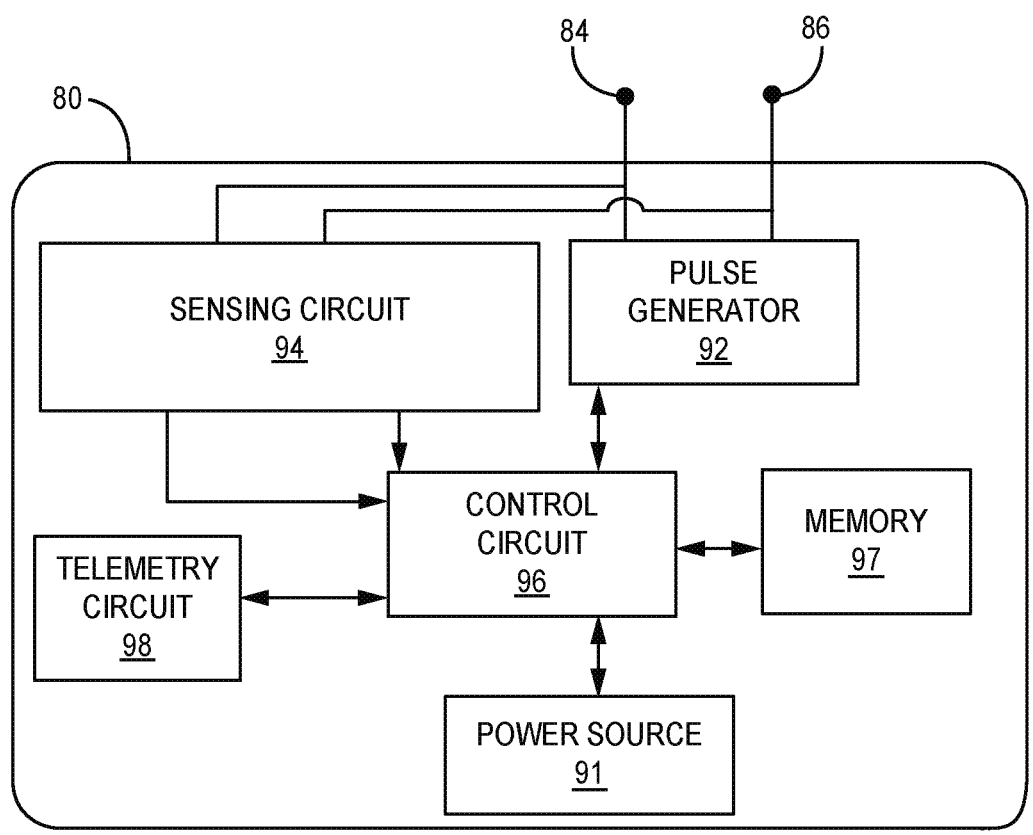
FIG. 4 is a schematic diagram of a pacemaker that may be co-implanted with a VAD and configured to operate in a VAD mode according to one example.

FIG. 4 is a functional block diagram of an example configuration of pacemaker 80 shown in FIGS. 1A and 1B. Pacemaker 80 includes a power source 91, pulse generator 92, a sensing circuit 94, a control circuit 96, memory 97, and telemetry circuit 98. The functions attributed to pacemaker 100 (or ICD 14) herein may be embodied as one or more processors, controllers, hardware, firmware, software, or any combination thereof. Power source 91 provides power to each of the other circuits and components of pacemaker 80 as required. Power source 91 may include one or more energy storage devices, such as one or more rechargeable or non-rechargeable batteries. The connections between power source 91 and other pacemaker circuits and components are not shown in FIG. 4 for the sake of clarity.

Pulse generator 92 generates electrical stimulation pulses that are delivered to heart tissue via electrodes 84 and 86. Electrodes 84 and 86 may be housing-based electrodes as shown in FIGS. 1A and 1B, but one or both electrodes 84 and 86 may alternatively be carried by an insulated, electrical conductor extending away from the pacemaker housing. Pulse generator 92 may include one or more low voltage capacitors and a charging circuit to charge the capacitor(s) to a programmed pacing pulse voltage under the control of control circuit 96. At appropriate times, as controlled by control circuit 96, the capacitor is coupled to electrodes 84 and 86 to discharge the capacitor voltage and thereby deliver the pacing pulse.

Control circuit 96 controls pulse generator 92 to deliver a pacing pulse in response to expiration of a pacing escape interval according to programmed therapy control parameters stored in memory 97. A pace timing and control circuit included in control circuit 96 may include an escape interval timer or counter that is set to a pacing escape interval used for controlling the timing of pacing pulses relative to a paced or sensed event (e.g., an R-wave). Upon expiration of a pacing escape interval, a pacing pulse is delivered. If a cardiac event is sensed during the pacing escape interval by sensing circuit 94, the scheduled pacing pulse may be inhibited, and the pacing escape interval may be reset to a new time interval. In some examples, pacemaker 80 delivers ventricular pacing during the VAD mode to provide pacing support for mitigating the effects of heart failure and promote adequate filling of blood pump 101.

In response to detecting a ventricular tachyarrhythmia, e.g., using the RRI-based detection criteria described in the above-incorporated U.S. Pat. No. 9,808,637, control circuit 96 controls pulse generator 92 to deliver one or more sequences of ATP pulses according to a programmed therapy regime. ATP sequences may include burst, ramp, burst plus ramp or other ATP pulse patterns. For example, an ATP burst sequence may be delivered including 6 to 10 pacing pulses delivered at pacing pulse intervals that are shorter than up to 97% of the detected RRIs. The amplitude of the ATP pulses may be set to a safety margin above a previously determined pacing capture threshold or at a nominal amplitude, e.g., up to 5 volts, that is expected to capture the ventricles with a high degree of certainty. For example, a typical ATP therapy may be a burst of 8 pulses delivered at 88% of the detected RRI cycle length, with each pulse having an amplitude of 5 volts. If VT is redetected, another sequence of ATP pulses may be delivered, e.g., at shorter intervals than the first sequence. As described below in conjunction with FIGS. 6 and 7, ATP control parameters may be adjusted in a VAD operating mode.

Sensing circuit 94 receives cardiac electrical signals developed across electrodes 84 and 86. A cardiac event may be sensed by sensing circuit 94 when the cardiac electrical signal crosses a sensing threshold, which may be an auto-adjusting sensing threshold. In response to a sensing threshold crossing, sensing circuit 94 passes a sensed event signal to control circuit 96 for use in controlling the timing of pacing pulses. Control circuit 96 receives R-wave sensed event signals from sensing circuit 94 and determines RRIs as the intervals occurring between consecutive R-wave sensed event signals. Tachyarrhythmia detection criteria may be applied to the determined RRIs to detect ventricular tachyarrhythmia according to implemented detection algorithms. Control parameters used to control tachyarrhythmia detection may be adjusted during the VAD operating mode.

Memory 97 may include computer-readable instructions that, when executed by control circuit 96, cause control circuit 96 to perform various functions attributed to pacemaker 80. The computer-readable instructions may be encoded within memory 97. Memory 97 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media. Memory 97 stores timing intervals, counters, or other data used by control circuit 96 to control the delivery of pacing pulses by pulse generator 92. Memory 97 may store control parameters that are adjusted for controlling pacemaker functions during a VAD mode.

Telemetry circuit 98 includes a transceiver and antenna for transferring and receiving data from external device 40 via a radio frequency (RF) communication link as described above. Pacemaker 80 may receive pacing and sensing control parameters via telemetry circuit 98 and store the control parameter values in memory 97 for access by control circuit 96. ATP therapy parameters, such as ATP type (e.g., burst, ramp, ramp plus burst, etc.), number of pulses, number of ATP sequences, etc., may be received by telemetry circuit 98 from external device 40.

A VAD mode command may be received by telemetry circuit 98 from external programmer 40 for causing pacemaker 80 to switch to the VAD mode. A normal, non-VAD mode command may be received by telemetry circuit 98 from external programmer 40 to switch pacemaker 80 back to the normal, non-VAD mode, e.g., if the VAD is removed. In some examples, pacemaker 80 may be configured to receive a notification signal from ICD 14 or VAD 100 via telemetry circuit 98 to indicate the presence of VAD 100 and/or confirm the presence of VAD 100 on a periodic basis. Upon receipt of an initial notification or command indicating the presence of VAD 100, pacemaker 80 may be configured to adjust a ventricular tachyarrhythmia detection parameter, a pacing therapy control parameter, an alert control parameter and/or a monitoring parameter as described below in conjunction with the accompanying flow charts.

Pacemaker 80 may transmit data, such as cardiac electrical signal data, and in particular signal data associated with detected ventricular tachyarrhythmia episodes, to external device 40. Transmitted data may be reviewed by a clinician or technician for use in monitoring the occurrence of sustained ventricular tachyarrhythmia episodes, programming tachyarrhythmia detection parameters, and programming pacing therapies delivered by pacemaker 80. In examples where pacemaker 80 is co-implanted with ICD 14, pacemaker 80 may transmit signals to ICD 14 via telemetry circuit 98 to confirm tachyarrhythmia detection and/or ATP delivery. In other examples, pacemaker 80 may signal ICD 14 that ventricular tachyarrhythmia has been detected and/or that ATP therapy is imminent, being delivered or completed.

Figure 5:
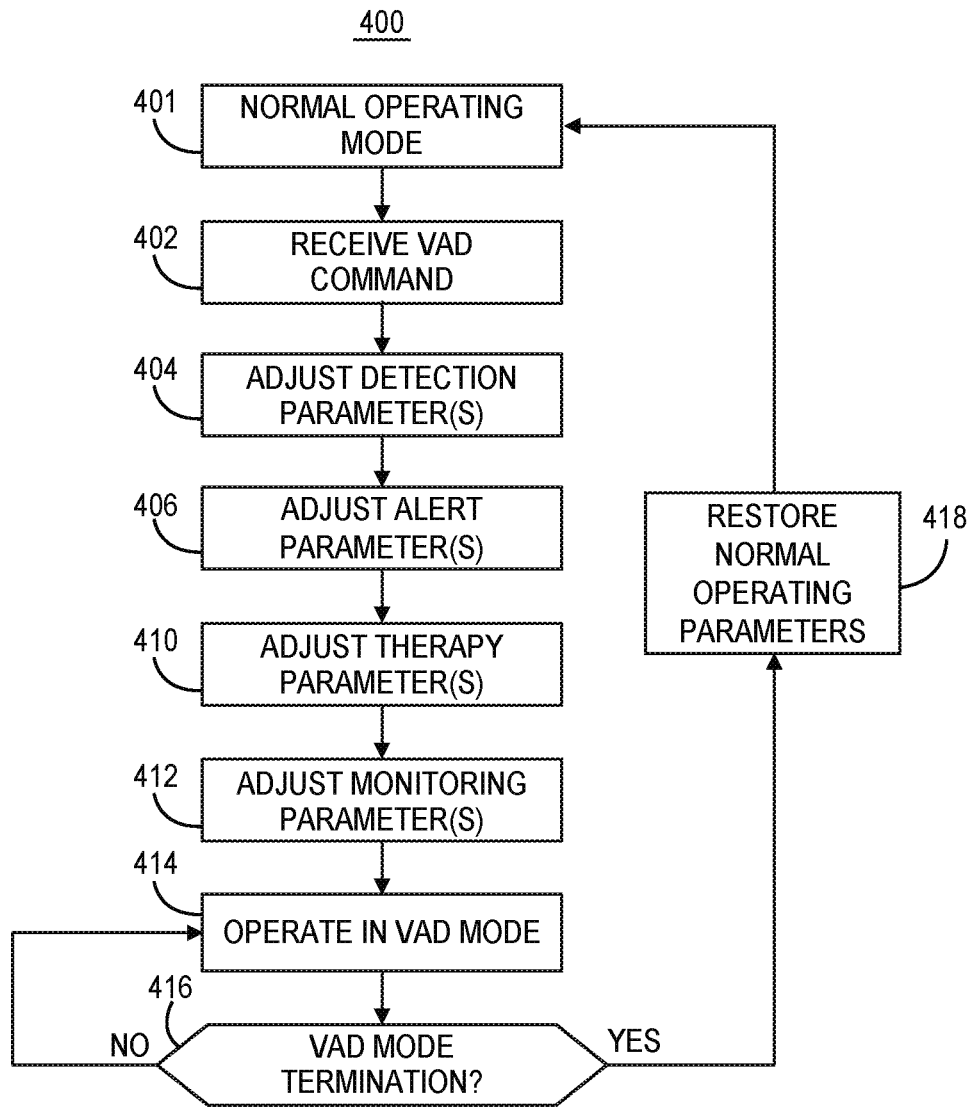
FIG. 5 is a flow chart of a method performed by an ICD according to one example.

FIG. 5 is a flow chart 400 of a method performed by a cardiac rhythm management device according to one example. The methods depicted in flow chart 400 and other flow charts presented herein are described primarily with reference to ICD 314. It is to be understood, however, that these methods or aspects of these methods may be performed by an ICD, pacemaker, or other cardiac rhythm management device, such as pacemaker 80 as an example.

ICD 314 may be initially configured in a non-VAD operating or "normal" operating mode at block 401. ICD 314 may be implanted in a patient prior to VAD 100 being implanted and may operate in the normal, non-VAD mode according to default and user-programmable control parameters and algorithms for detecting cardiac arrhythmias and delivering electrical stimulation therapies automatically as needed to treat the arrhythmias. In other examples, the ICD 314 may be implanted concomitantly or secondarily to VAD 100. In these cases, ICD 314 may be initially configured in a normal, non-VAD, operating mode at block 401 at the time of device manufacture but may be programmed to switch to a VAD mode if being co-implanted with VAD 100.

At block 402, ICD 314 receives a VAD mode command from another medical device. The other device may be an external programmer, e.g., external programmer 40 shown in FIG. 1A, or an external controller of the VAD 100, e.g., controller 110 shown in FIG. 1A. The VAD command indicates co-implantation of a VAD with ICD 314 in a patient. Control circuit 380 may receive the VAD command indicating the presence of a co-implanted VAD 100 via telemetry circuit 388. Control circuit 380 switches from the normal, non-VAD operating mode to the VAD mode in response to receiving the VAD command by automatically adjusting one or more control parameters used to control the operation of ICD 314 during the VAD mode. The one or more control parameters may include a tachyarrhythmia detection parameter, a therapy control parameter, criteria for generating an alert, and/or a control parameter used for monitoring the cardiac electrical signal received by sensing circuit 386 and/or one or more physiological sensor signals produced by sensors 396 for detecting a change in a physiological condition of the patient.

In some examples, ICD 314 switches from the normal, non-VAD operating mode to the VAD mode of operation by adjusting one or more tachyarrhythmia detection control parameters at block 404. The tachyarrhythmia detection control parameters may be adjusted by decreasing a VT and/or VF interval range and/or increasing the VT and/or VF NID, as examples. The adjustments to detection control parameters may increase a ventricular rate threshold (e.g., by decreasing an RRI threshold that is detected as a VT or VF interval) so that slowest tachyarrhythmia detected in the VAD mode is required to be faster than the slowest tachyarrhythmia detectable in the non-VAD mode. In this way, a relatively slow VT may go undetected since therapy delivery may not be critical when the patient is supported by VAD 100. Adjustments to the detection control parameters may include delaying detection. The minimum time required to detect a relatively fast VT or VF may be increased by increasing the NID and/or increasing a number of cardiac signal time segments required to be classified as VT or VF allowing more time for the tachyarrhythmia episode to spontaneously terminate. A tachyarrhythmia may be required to be sustained for a longer time period before detection is made as compared to the normal, non-VAD mode.

In some examples, detection control parameters are adjusted at block 404 to enable detection of VT or VF over sustained periods of time when anti-tachyarrhythmia therapy is withheld. For instance, a redetection algorithm may be performed at predetermined time intervals after an initial VT or VF detection and continue until the VT or VF spontaneously terminates and/or therapy is delivered and the rhythm is terminated. In other examples, once an initial detection is made, if therapy is not delivered, continuous re-detection of the VT or VF episode may be ongoing based on beat-by-beat analysis or other cardiac signal segment based analysis of the cardiac electrical signal(s) received by sensing circuit 386. In this way, a VT or VF episode may be detected as a sustained VT or VF episode that persists for minutes, hours or even days, based on intermittent or continuous re-detection of an untreated (or unsuccessfully treated) VT or VF episode.

At block 406, control circuit 380 may adjust patient and/or clinician alert control parameters. For example, as described below, automatic therapies may be disabled in the VAD mode. In this case, an alert may be generated by control circuit 380 in response to detecting a VT or VF episode for which an automatic therapy that would normally be immediately scheduled during the normal, non-VAD mode of operation of the ICD 314. The alert may include a patient alert to enable the patient to manually schedule a therapy or seek medical attention. The alert may include a physician alert that is transmitted to the patient's physician so that the physician or a medical center may contact the patient for follow up. By generating an alert, a CV/DF shock therapy may be scheduled to occur in a clinical setting to reduce anxiety and risk of injury to the patient.

In other examples, alert control parameters may include enabling patient and/or physician alerts to be generated in response to a threshold duration of a sustained tachyarrhythmia episode detection, detecting a worsening of a tachyarrhythmia episode (e.g., acceleration or deterioration to a more severe type of tachyarrhythmia), and/or failed therapy attempts. In some cases, an alert that is enabled during the normal, non-VAD operating mode may be disabled. For example, a patient alert of a tachyarrhythmia detection may be disabled but a clinician alert may be enabled to allow the clinician to select a course of action without creating undue patient anxiety. As such, alert control parameters adjusted at block 406 upon receiving a VAD mode command may include enabling, adjusting and/or disabling alerts that are automatically generated during the normal, non-VAD operating mode and/or enabling new alerts that are not available or used during the non-VAD operating mode. As an example, a patient or physician alert that a shockable VT or VF rhythm detection has been made but automatic therapy is disabled may be enabled to be generated during the VAD mode, but no such alert is available during the non-VAD operating mode.

At block 410, control circuit 380 may respond to the VAD mode command by automatically adjusting therapy delivery control parameters. In some examples, automatic therapies are disabled in the VAD mode. In this way, a CV/DF shock is not delivered to the patient unexpectedly, because the patient may be adequately supported hemodynamically by VAD 100. When automatic therapies are disabled, a patient or clinician may manually schedule the therapy to occur at a specified time. For example, an alert may be generated according to the adjusted alert control parameters set at block 406 to notify the clinician or patient that VT or VF is being detected. Using external programmer 40, a user may enter a time of day for delivering a shock therapy or manually select to deliver a shock therapy without delay. For instance, a shock therapy may be scheduled to occur at a later time of day or remain unscheduled, but if the patient becomes symptomatic, the patient or a caregiver may be able to schedule an immediate therapy. A CV/DF shock may be scheduled manually by a user so that if the VT or VF episode is sustained until a scheduled CV/DF shock delivery time, one or more CV/DF shocks are delivered. For instance, user may manually schedule CV/DF shocks to occur only at night when the patient is expected to be sleeping with a reduced risk of injury, e.g., due to falling.

In some cases, some automatic therapies are disabled in the VAD mode at block 410, but other therapies may remain enabled or even scheduled to be delivered earlier and/or more frequently. For example, in response to VT or VF detection, an automatic CV/DF shock may be disabled, but ATP may remain enabled. A maximum number of ATP attempts may be increased and/or a progression of more aggressive or different types of ATP therapies may be scheduled.

In other examples, an automatic therapy, such as CV/DF shock therapy, may remain enabled in the VAD mode but is scheduled to occur after a delay from a time of VT/VF detection. Control circuit 380 may automatically schedule CV/DF shocks to occur only at specified time(s) of day and may limit the maximum number of attempted shocks per day. For example, control circuit 380 may schedule a CV/DF shock to occur only between 3:00 am and 4:00 am or another default or user-specified time and may schedule as few as one shock per twenty-four hours. In this way, therapy is still automatically scheduled in response to detecting a VT or VF rhythm, but the CV/DF shock is delayed until a time that the patient is expected to be asleep and risk of injury is minimized. A clinician and/or patient alert may be enabled at block 406 to alert the clinician and/or patient of the pending therapy that is scheduled.

At block 412, control circuit 380 may adjust one or more patient monitoring parameters. During the VAD mode, the patient may experience a worsening tachyarrhythmia or become symptomatic if the hemodynamic support by VAD 100 is insufficient. For example, VAD 100 may experience a low flow or suction event if the flow input from the left ventricle is too low during VT or VF. As such, additional patient monitoring algorithms may be enabled during the VAD mode, particularly when a VT or VF therapy is being withheld or delayed. Ongoing monitoring of the cardiac rhythm may be enabled in order to detect a potentially worsening rhythm and enable scheduling of a delayed or withheld therapy to terminate the worsening rhythm. Other monitoring of a physiological signal or patient condition may be enabled or adjusted during the VAD mode in order to detect an indication that a therapy is needed. For example, monitoring for myocardial ischemia based on T-wave changes, monitoring for a relative decrease in blood or tissue oxygen saturation using an oxygen sensor, monitoring for respiratory changes using acoustical sensors or impedance sensors, change in body temperature using a temperature sensor, and/or monitoring patient activity and/or patient posture using an accelerometer may be performed in order to detect a possible worsening in a condition of the patient that warrants an alert (patient and/or clinician) and/or more immediate therapy delivery.

At block 414, control circuit 380 controls operation of the ICD 314 in the VAD mode according to at least one adjustment made to control parameters in at least one of blocks 404, 406, 410 and 412. Adjustments to the control parameters may include automatic adjustments made in response to the VAD mode command and may include manually adjusted control parameters programmed by a user using external programmer 40. While FIG. 5 shows adjustments being made to detection parameters (block 404), alert parameters (406), therapy parameters (410) and monitoring parameters (412), it is to be understood that adjustments at all of blocks 404 through 412 are not required for switching to a VAD mode. At least one control parameter is adjusted at one block 404 through 412, and one or more parameters may be adjusted at one or more of blocks 404 through 412 for switching to the VAD mode.

At block 416, ICD 314 may determine that the VAD mode should be terminated and switch to the non-VAD, normal operating mode at block 418 by restoring the normal operating parameters. In some examples, once the VAD mode is enabled, the VAD mode becomes the "permanent" operating mode of the ICD 314 in that control circuit 380 may only switch back to the set of control parameters used during the normal non-VAD operating mode in response to receiving a user command from another device. ICD 314 may not be configured to automatically switch from the VAD mode back to the normal, non-VAD mode without receiving a command from another device. If ICD 314 receives a "normal" command at block 416, e.g., from external programmer 40, indicating that a VAD is no longer co-implanted with ICD 314 or that the VAD mode should be disabled, control circuit 380 may respond by switching to the normal non-VAD operating mode by restoring the most recently used non-VAD mode operating control parameters at block 418.

In other examples, ICD 314 may determine at block 416 that the VAD operating mode should be terminated due to an absence of VAD communication signals for a pre-determined time interval. For instance, VAD 100 may be configured to transmit a notification signal to ICD 314 on a periodic basis, e.g., daily, weekly or monthly, confirming the presence and functionality of VAD 100. VAD 100 may transmit the periodic notification signal by pinging ICD 314 or in response to a periodic request signal transmitted from ICD 314 to VAD 100. If a periodic notification signal is not received from VAD 100, ICD 314 may determine the VAD mode should be terminated at block 416 and restore the normal, non-VAD operating mode parameters at block 418.

Figure 6:
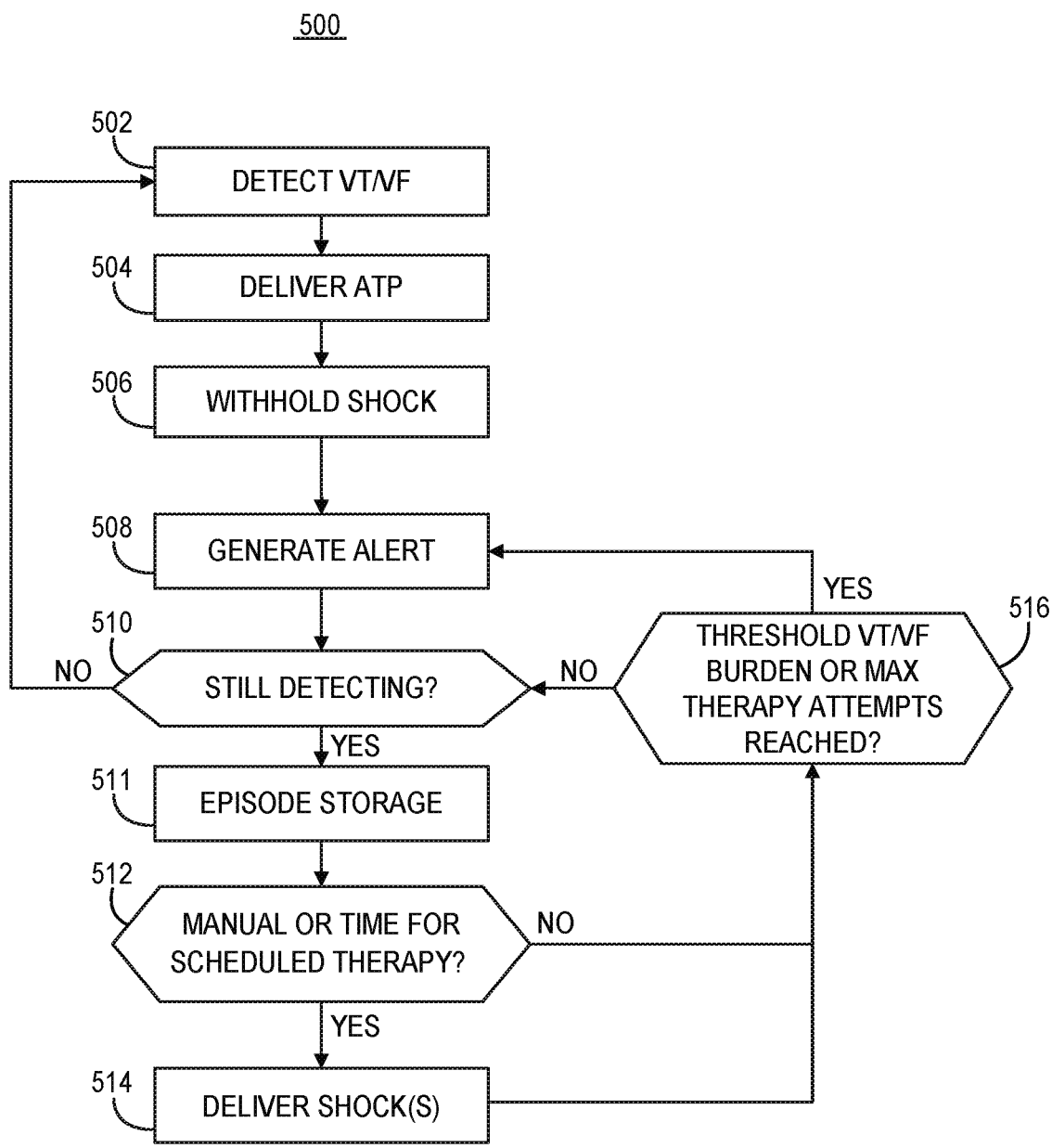
FIG. 6 is a flow chart of a method performed by an ICD operating in a VAD mode according to one example.

FIG. 6 is a flow chart 500 of a method performed by ICD 314 operating in a VAD mode according to one example. After switching to the VAD mode of operation, control circuit 380 may detect a ventricular tachyarrhythmia (VT or VF) at block 502. Detection of the VT or VF may be based on RRIs and/or cardiac electrical signal morphology analysis, as in the normal, non-VAD operating mode. In some instances, however, detection control parameters may be adjusted in the VAD mode to be different than the normal, non-VAD operating mode. For example, the NID or threshold number of RRIs counted as VT or VF intervals required to detect VT or VF may be increased, the maximum RRI counted as a VT interval or as a VF interval may be decreased or other thresholds or criteria may be defined differently for VT/VF detection during the VAD mode compared to the normal, non-VAD operating mode. In some examples, the VT/VF detection parameters may be adjusted such that detection sensitivity is decreased or requires a longer time to reach detection criteria. In other examples, tachyarrhythmia detection control parameters may be unchanged from the normal, VAD operating mode.

After detecting the VF or VF, control circuit 380 may control therapy delivery circuit to deliver ATP according to ATP therapy parameters programmed in the VAD mode. For example, ATP may be used following all VT or VF detections and/or a maximum number of ATP therapy attempts may be greater than the number of attempts made during the non-VAD operating mode. If unsuccessful in terminating the detected VT or VF, ATP may be repeated at scheduled intervals of time or a predetermined number of times per day as long as the VT or VF is still being detected. In some examples, control circuit 380 may monitor the cardiac rhythm to detect a slowing, increased regularity or other change in the detected tachyarrhythmia and control therapy delivery circuit 384 to deliver ATP in response to detecting the change in the tachyarrhythmia. In other examples, ATP control parameters may be unchanged compared to the non-VAD operating mode. ATP may be programmed to be delivered as a first therapy attempt for VT and/or VF.

At block 506, control circuit 380 withholds an automatic CV/DF shock that would be delivered in response to the VT or VF detection during the normal non-VAD operating mode (and any delivered ATP failed to terminate the VT or VF). At block 508, control circuit 380 may control telemetry circuit 388 and/or alert circuit 394 to generate an alert to notify a clinician and/or the patient that a shock therapy is being withheld and that VT or VF that would normally be treated by a shock therapy (in the non-VAD mode) has been detected. Control circuit 380 may continuously (beat-by-beat) or periodically determine if the VT or VF detection criteria are still being satisfied at block 510. For example, after a predetermined time interval or number of RRIs, the detection criteria used for the initial VT or VF detection or different, redetection criteria may be applied to RRIs and/or cardiac signal morphology analysis to determine if the VT or VF episode is sustained. If sustained, control circuit 380 may store a cardiac signal segment in memory 382 at block 511 to provide a clinician with a historical record of the sustained episode. A cardiac signal segment may be stored at block 511 periodically, as long as the episode is still being detected, and may not be stored every time the episode is redetected. In some examples, ATP may be attempted periodically during the sustained VT or VF, and control circuit 380 may determine if the VT or VF is still being detected after each ATP attempt.

The shock therapy that is withheld at block 506 at the time of VT/VF detection may be scheduled to occur at a predetermined time of day, e.g., during the night or when the patient is expected to be asleep, which may be a programmable time of day. In other examples, the shock therapy that is withheld at block 506 may be delivered after a predetermined maximum VT or VF episode duration has been reached. For example, the VT or VF episode may be detected for up to one hour, up to four hours, up to eight hours, up to twelve hours or up to 24 hours. Control circuit 380 determines at block 512 if a maximum delay of a shock therapy or a specified time of day has been reached. If a withheld shock is scheduled to occur at a specified time of day or after a predetermined delay (e.g., a specified maximum episode duration), control circuit 380 may verify that the VT or VF is still being detected then deliver the delayed shock at block 514. In some instances, a patient or clinician may manually schedule a shock that was withheld at block 506 using the external programmer 40. Upon receiving a "shock now" command, control circuit 380 controls therapy delivery circuit 384 to deliver the withheld shock at block 514 after verifying that the VT or VF episode is still being detected.

The shock may be delivered at block 514 at either a scheduled time of day, after a predetermined time delay, or in response to a manually entered shock command using the same shock pulse parameters, such as shock energy and pulse shape, as the pulse parameters programmed for use during the normal non-VAD operating mode. In other examples, the control parameters defining the shock pulse energy and shape may be programmed differently during the VAD mode than during the normal non-VAD mode. If the shock therapy is successful, control circuit 380 no longer detects the VT or VF episode at block 510 and returns to block 502 to continue monitoring the cardiac electrical signals to detect VT/VF according to the VAD mode of operation.

In some examples, at block 516, the control circuit 380 may determine if a threshold VT or VF burden has been reached. The threshold VT/VF burden may be a total time interval threshold during which the patient has been determined to be in a sustained VT or VF episode, either based on continuous (beat-by-beat) or intermittent but consecutive VT/VF re-detections. In other examples the VT/VF burden threshold may be reached when the total time duration of one or more VT/VF episodes reaches a time interval threshold. In still other examples, a maximum number of therapy attempts may be reached if a threshold number of ATP attempts and/or CV/DF shocks have been delivered without terminating the VT or VF episode. If a threshold VT/VF burden or maximum number of therapy attempts is reached, an alert may be generated at block 508. The alert may notify a medical professional and/or the patient to indicate that medical intervention may be necessary.

Figure 7:
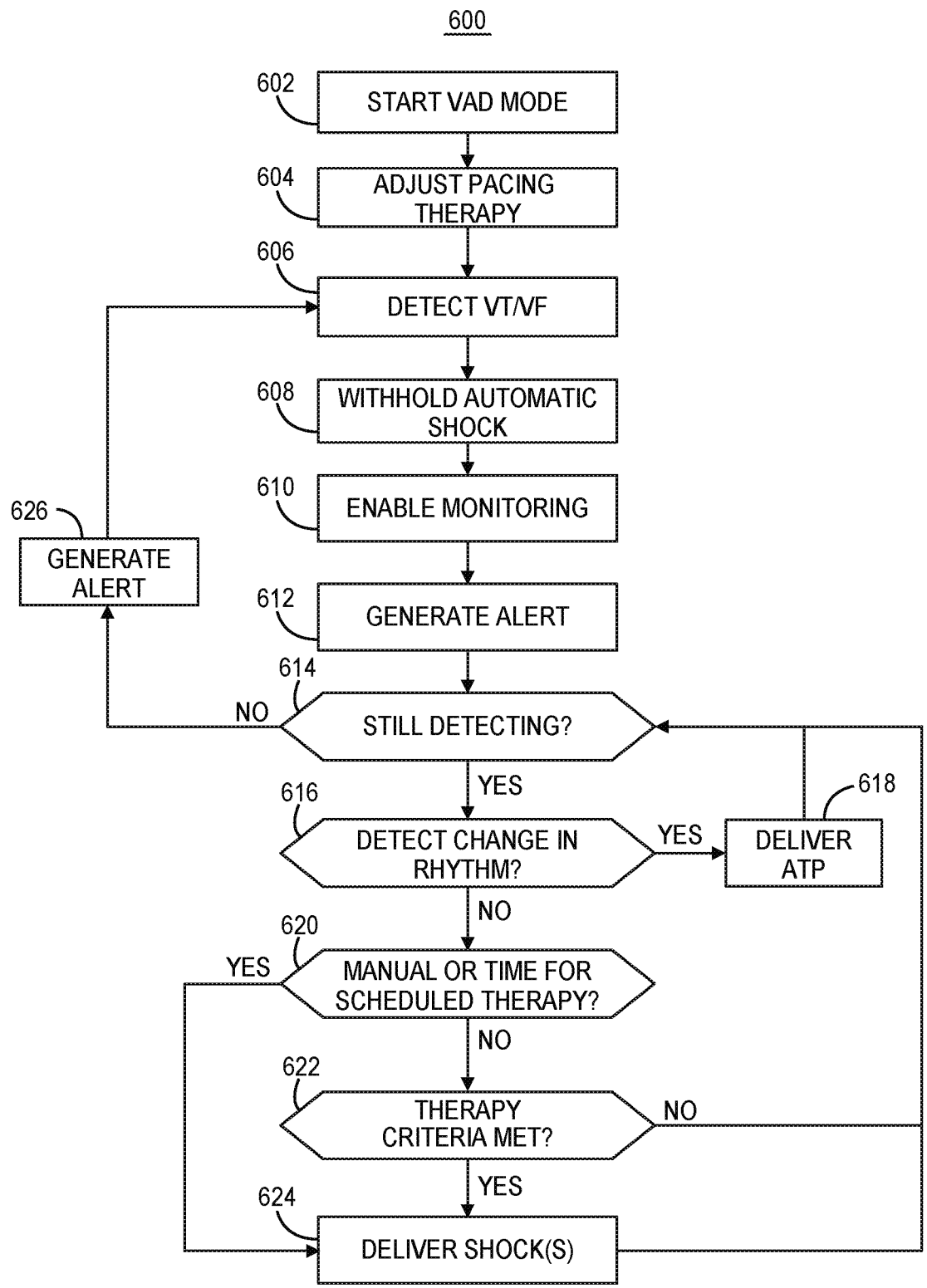
FIG. 7 is a flow chart of ICD operation during the VAD mode according to another example.

FIG. 7 is a flow chart 600 of ICD operation during the VAD mode according to another example. At block 602, ICD 314 is programmed to operate in the VAD mode. Automatic and user-programmable adjustments to operating control parameters are made by control circuit 380 for switching to the VAD mode as described above. In response to receiving the VAD mode command, control circuit 380 may also automatically adjust one or more pacing therapies at block 604. For example, if the ICD 314 is configured to provide CRT using a coronary sinus lead for delivering left ventricular pacing, the left ventricular pacing feature may be disabled at block 604. In other examples, RV pacing may be enabled at block 604. RV pacing may be enabled to support RV function in the presence of VAD 100 and mitigate RV failure. A dual chamber or atrial pacing mode may be enabled to provide pacing support in the presence of VAD 100. A pacing mode that is programmed or enabled during the normal, non-VAD mode may be disabled or adjusted to a different pacing mode during the VAD mode at block 604.

When VT or VF is detected at block 606 during the VAD mode, an automatic shock that would be delivered during the normal non-VAD mode may be withheld at block 608. At block 610, control circuit 380 may enable monitoring functions to monitor one or more conditions of the patient during the detected VT or VF that is not immediately treated by delivering a shock therapy. As described above, ICD 314 may include one or more physiological sensors for producing a signal correlated to a physiological condition of the patient. The cardiac electrical signal and/or one or more physiological sensor signals may be monitored for detecting a worsening condition of the patient. For instance, a worsening of the cardiac rhythm (e.g., acceleration of the VT rate) and/or a worsening of a hemodynamic condition of the patient may be detected by enabling monitoring at block 610.

As described above, an alert may be generated at block 612 when VT or VF is detected. A clinician may be alerted without alerting the patient in some examples. If the VT or VF episode is still being detected at block 614 control circuit 380 may determine if the episode is changing, e.g., in rate and/or regularity, at block 616 by analyzing the cardiac electrical signal(s) received from sensing circuit 386. For example, RRIs may continue to be monitored beat-by-beat or intermittently after the initial VT or VF detection to detect a decrease in RRIs indicating that the tachyarrhythmia is accelerating. An accelerated rhythm may be detected based on a shorter median RRI since the initial detection, for example. The median RRI may be determined out of a most recent predetermined number of RRIs, e.g., the most recent 12 to 18 RRIs. Control circuit 380 may control therapy delivery circuit 384 to deliver ATP at block 618 if an accelerated rhythm is detected at block 616.

In other examples, ATP may be delivered in response to detecting a rate deceleration based on an increased median RRI. In still other examples, RRI variability may be determined over a predetermined number of RRIs, e.g., by determining differences between pairs of RRIs or a difference between each RRI and a median RRI. ATP may be delivered if a change in RRI variability is detected. ATP may be delivered at block 618 in response to a change in the detected VT or VF episode that indicates acceleration, deceleration, a change in regularity (e.g., less variability or more variability in RRIs) or other rhythm change, as long as VT or VF is still being detected. Delivering ATP at block 618 may include one or more attempts at delivering ATP, which may include different ATP therapies, e.g., different coupling intervals, different inter-pulse intervals, burst ATP, ramp ATP, etc.

If the VT or VF episode is still being detected at block 614 after attempting ATP, and if an accelerating rhythm is not detected at block 616, control circuit 380 may wait to deliver a shock at block 624 until a shock is manually scheduled by a user or until a specified time of day or a predetermined shock delay has expired ("yes" branch of block 620). If an immediate shock is not manually scheduled and the time for a delayed, scheduled shock is not yet reached ("no" branch of block 620), control circuit 380 may determine if other therapy criteria are met at block 622. Other criteria for triggering therapy delivery may be applied to the cardiac electrical signal and/or other physiological signals being monitored. For example, an indication of resting patient activity, non-upright posture, ischemia based on changes in T-waves in the cardiac electrical signal, low oxygen saturation of blood or tissue based on an optical sensor, or other detected condition may satisfy therapy delivery criteria at block 622 causing control circuit 380 to control therapy delivery circuit 384 to deliver a shock at block 624. If other therapy criteria are not met, at block 622, control circuit 380 continues monitoring the VT/VF episode at block 614.

Anytime the VT or VF rhythm is no longer detected at block 614, which may follow ATP, a shock, or spontaneous termination, control circuit 380 may generate an alert to notify the patient and/or medical personnel that the tachyarrhythmia is terminated at block 626. Control circuit 380 returns to block 606 to await the next VT or VF episode detection.

Figure 8:
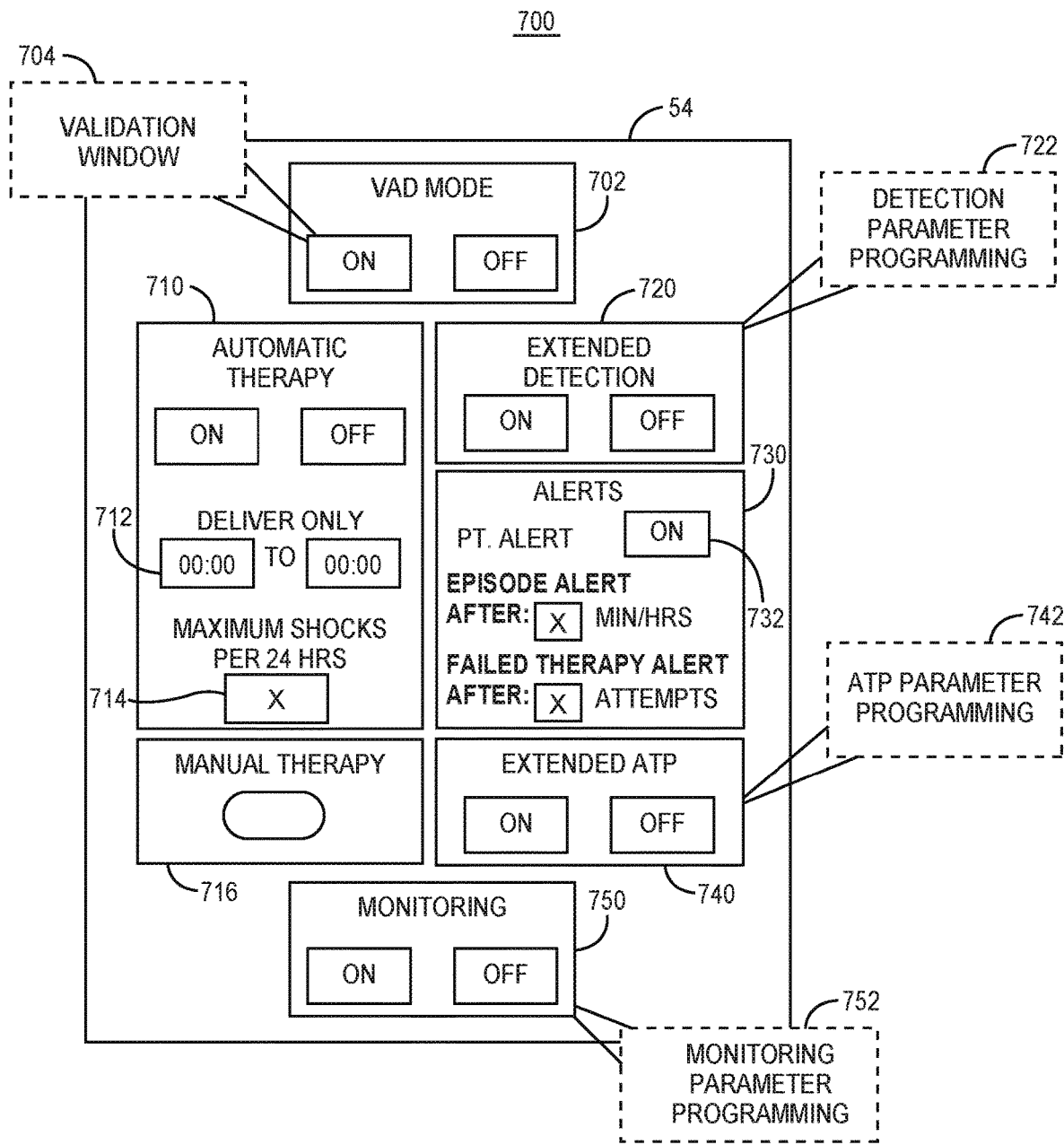
FIG. 8 is a conceptual diagram of a user interface that may be generated by a processor of external programmer for display to a user for programming a VAD mode.

FIG. 8 is a conceptual diagram of a user interface 700 that may be generated by processor 52 of external programmer 40 for display to a user on display 54. The user interface 700 may include a VAD mode programming window 702 that enables a user to program the VAD mode "on" or "off." If the "on" button is selected, a validation screen or pop-up window 704 may appear requiring the user to enter authentication data that verifies the presence of a VAD co-implanted in the patient with the ICD being programmed. For example, window 704 may prompt the user to enter a VAD model and/or serial number, a date of VAD implant, or other information specific to the VAD co-implanted in the patient to authenticate its presence and the appropriateness of the ICD operating in the VAD mode.

In some examples, the VAD mode, once programmed "on," includes default control parameters for arrhythmia detection, therapy delivery, alert generation and/or patient monitoring that are automatically set by control circuit 380 upon receipt of the VAD mode command from external programmer 40. In other examples, one or more control parameters used by control circuit 380 for controlling ICD operations during the VAD mode may be programmable by a user interacting with user interface 700.

In the example shown in FIG. 8, a user may turn automatic shock therapy on or off using automatic therapy window 710 of interface 700. If automatic shock therapy is turned off, a user may control ICD 314 to deliver a shock manually using the manual therapy button 716. For instance, as described in conjunction with the flow chart 500, VT or VF may be detected and, if automatic shocks are disabled or turned "off," an alert may be generated so that the patient (or a clinician during an office visit) may manually control the ICD 314 to deliver the shock therapy at a time selected by the patient. This allows the patient to seek assistance or medical supervision as needed and be prepared for the shock therapy. As such, in some examples, upon detecting a VT or VF and withholding shock therapy, processor 52 may generate an alert screen on interface 700 including a display of manual therapy button 716.

If a user enables automatic shock therapies by selecting the "on" button of the automatic therapy window 710, the processor 52 of external programmer 40 may enable other programmable parameters 712 and 714 of window 710 for programmability. These programmable parameters 712 and 714 allow automatic shocks to be scheduled according to user programmed control parameters during the VAD mode. In the example shown, automatic shock therapy may be withheld at the time of VT or VF detection as described above unless the detected VT or VF persists until a programmed time of day 712. The time of day 712 for shock delivery may be programmable as a start time and an end time that are entered by the user. To illustrate, a user may select an automatic shock delivery time interval from 2:00 am to 4:00 am, when the patient is expected to be in bed and asleep. If VT or VF is detected outside the programmed time of day 712, the shock therapy is withheld until the programmed time of day 712 and delivered during the programmed time of day 712 as long as the tachyarrhythmia episode is still being detected. In other examples, instead of or in addition to a programmed time of day 712, a maximum VT/VF episode delay interval may be a user programmable parameter that may be included in automatic therapy window for programming a maximum number of minutes or hours the detected VT or VF rhythm is allowed to persist before a shock therapy is delivered.

Additionally or alternatively, the automatic therapy window 710 may include a programmable maximum number of shocks parameter 714. In the example shown, the maximum number of shocks may be specified per twenty-four hour period. In this way, a user may limit both the time at which shocks can occur and the number of shocks that can be delivered over a given time period during the VAD mode. For example, a user may limit the number of shocks to be a maximum of one shock per twenty-four hours. If the shock fails to terminate the VT or VF rhythm, the next shock attempt may be made according to the programmed time of day 712 on the next day. This allows the patient to consult with his/her physician before another shock attempt is made.

An extended detection window 720 may be included in user interface 700 to enable a user to turn extended detection on or off. When turned off, VT and VF detection algorithms may be performed according to the same control parameters and detection criteria as those used during the normal, non-VAD mode. When turned on, the VT and/or VF detection times may be extended by increasing the NID, increasing a number of cardiac electrical signal time segments required to be classified as VT or VF, or otherwise modifying the detection algorithm so that VT or VF is detected relatively later after the onset of the VT or VF episode than the detection time during the normal, non-VAD mode.

The adjustment of one or more detection control parameters or criteria may be made automatically upon turning extended detection on. In some examples, some detection control parameters used during extended detection may be user programmable parameters. As such, a detection parameter programing window 722 may be displayed on user interface 700 in response to the user selecting the "on" button of the extended detection window 720. Examples of programmable extended detection control parameters may include the NID for detecting VT, the NID for detecting VF, the number of cardiac electrical signal segments required to be classified as VT/VF, VT and VF interval ranges (of RRIs), and/or a minimum time interval for detecting a sustained VT or VF.

User interface 700 may include an alert window 730 for enabling or disabling a patient alert 732. In some instances, the patient alert may be silenced or disabled such that only a clinician or medical personnel are alerted when an alert condition is satisfied during the VAD mode. Alert conditions may be set automatically by control circuit 380; however, in some examples alert conditions may include user-programmable alert conditions. For example, as shown in FIG. 8, the alert window 730 may include enabling an alert when VT or VF episode has been sustained for a programmable threshold time interval (e.g., in minutes or hours). The threshold may be reached over a single sustained episode. In other examples, the threshold may be reached by summing the cumulative time durations of multiple VT or VF episodes in which case the threshold may be referred to as a VT or VF threshold "burden."

As another example of a programmable alert control parameter in the VAD mode, a user may program a failed therapy alert to be generated after a specified number of therapy attempts have been made followed by redetection of the VT or VF episode. The therapy attempts may include only ATP attempts, only shock attempts, or a combination of both (which may be separately programmable for generating one or separate alerts in various examples). The alert window 730 may include additional or different programmable alert control parameters than the specific examples shown here, which enable a user to program the conditions for which a patient alert is generated (or not) and the conditions for which a clinician alert is generated (or not). While not shown in FIG. 8, it is to be understood by the other examples of pop-up windows 704, 722, 742 and 752 that processor 52 may generate a new user interface window or pop-up window within user interface 700 in response to a user selecting a programmable parameter of alert window 730 to enable a user to program various control parameters used by control circuit 380 for generating alerts. In some examples, times of day for transmitting alerts to a clinician and/or patient may be programmable to avoid alerts being transmitted in the middle of the night, for example.

User interface 700 may include an extended ATP window 740 that enables a user to program ATP therapies to be delivered in response to a detected VT or VF more extensively than during the normal non-VAD mode. Since automatic shock therapy may be disabled or delayed during the VAD mode, the number of times ATP is attempted for terminating a detected tachyarrhythmia may be increased. More types of ATP may be attempted, e.g., ramp, burst, ramp plus burst, etc. The increased number of attempts may include adjustments of the coupling interval, used to synchronize the leading ATP pulse to a sensed R-wave and/or adjustments to the ATP time interval between consecutive ATP pulses. As such, "extended ATP" may generally refer to increased use of ATP following a VT or VF detection compared to the normal, non-VAD mode. The increased use of ATP may include scheduling one or more ATP therapies to occur immediately after the VT or VF episode detection and/or scheduling one or more ATP therapies to occur at specified time intervals delayed from the time of VT or VF detection, after one hour, after eight hours, etc. such that ATP may be repeated during a sustained VT or VF episode. In some examples, extended ATP may include triggering ATP delivery in response to detecting a change in the tachyarrhythmia.

Extended ATP may be programmed on by a user via window 740, and control circuit 380 may automatically adjust one or more ATP control parameter settings to increase the number of ATP therapies that will be attempted during a sustained VT or VF episode. As indicated in FIG. 8, processor 52 may generate a new or pop-up ATP parameter programming window 742 of user interface 700 in response to a user selecting "on" of the extended ATP window 740. A variety of ATP control parameters, as listed above, may be programmed for use by control circuit 380 for controlling ATP delivery during the VAD mode using window 742.

Monitoring window 750 is another window that may be included in user interface 700. Additional patient monitoring may be enabled during the VAD mode by selecting the "on" button of window 750. Control circuit 380 may automatically adjust one or more monitoring control parameters in response to monitoring being programmed on. In some examples, processor 52 generates a monitoring control parameter programming window 752 in user interface 700 to enable a user to program parameters that control patient monitoring performed during the VAD mode, which may be in addition to or alternatively to automatically adjusted monitoring control parameters. In one example, patient temperature monitoring is turned on when monitoring is enabled via window 750 and an automatic alert is generated if a patient's body temperature exceeds a threshold. Patients having a VAD implanted are at increased risk of infection, particularly when the VAD includes a percutaneous drive line. Temperature monitoring during the VAD mode may provide an early alert of a possible infection. Other examples of physiological signals discussed above may be enabled using monitoring window 750, such as ischemia monitoring, oxygen saturation monitoring, pressure monitoring or other physiological signals produced by sensors 396 included in ICD 314.

While a particular example of user interface 700 is shown, it is to be understood that various arrangements of one or more interactive windows, screens, tabs, pull down menus, or the like may be displayed in user interface 700 to enable a user to at least turn on or enable the VAD mode and may enable a user to program a variety of control parameters used by control circuit 380 during the VAD mode of operation of ICD 314. Once turned on, the ICD 314 does not automatically revert to the non-VAD mode unless the VAD mode is turned off using user interface 700 in some examples. Turning the VAD mode off may again require additional validation steps using window 704 in order to prevent inadvertent disabling of the VAD mode.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, an implantable cardiac rhythm management device that is co-implantable with a VAD and programmable for operating in a VAD mode has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:
1. An implantable medical device comprising:
a sensing circuit configured to receive a cardiac electrical signal produced by a heart of a patient;
a therapy delivery circuit configured to generate an electrical stimulation therapy for delivery to the heart of the patient;
a telemetry circuit configured to receive a command from another medical device indicating co-implantation of a ventricular assist device with the implantable medical device in the patient; and
a control circuit coupled to the sensing circuit, the therapy delivery circuit and the telemetry circuit and configured to:
operate in a first mode comprising detecting a cardiac arrhythmia from the cardiac electrical signal and controlling the therapy delivery circuit to automatically deliver the electrical stimulation therapy in response to detecting the cardiac arrhythmia; and
switch from operating in the first mode to operating in a second mode in response to receiving the command, wherein switching to the second mode comprises adjusting at least one control parameter used for controlling the electrical stimulation therapy and the control circuit is configured to operate in the second mode by:
detecting a tachyarrhythmia from the cardiac electrical signal;

delaying the electrical stimulation therapy in response to detecting the tachyarrhythmia; and generating an alert indicating that the tachyarrhythmia is detected and the electrical stimulation therapy is delayed.

2. The device of claim 1, wherein the control circuit is configured to adjust the at least one control parameter by disabling automatic delivery of the electrical stimulation therapy in response to detecting the cardiac arrhythmia during the second mode of operating.

3. The device of claim 1, wherein the control circuit is configured to adjust the at least one control parameter by scheduling the electrical stimulation therapy to occur at a scheduled time of day in response to detecting the cardiac arrhythmia during the second mode of operating.

4. The device of claim 1, wherein the control circuit is configured to:
detect the cardiac arrhythmia during the first mode as a first ventricular tachyarrhythmia episode;
control the therapy delivery circuit to deliver the electrical stimulation therapy as a shock therapy delivered automatically in response to detecting the first ventricular tachyarrhythmia episode;
detect the tachyarrhythmia from the cardiac electrical signal after switching to the second mode as a second ventricular tachyarrhythmia episode; and
in response to detecting the second ventricular tachyarrhythmia episode during the second mode, delaying the electrical stimulation therapy by withholding the shock therapy.

5. The device of claim 1, wherein the control circuit is configured to adjust the at least one control parameter by adjusting an anti-tachycardia pacing therapy control parameter.

6. The device of claim 1, wherein the control circuit is configured to adjust the at least one control parameter by adjusting a tachyarrhythmia detection control parameter that prolongs a minimum time required to detect a tachyarrhythmia during the second mode compared to the first mode.

7. The device of claim 1, wherein the control circuit is further configured to switch to the second mode by adjusting criteria for generating an alert during the second mode.

8. The device of claim 1, wherein the control circuit is configured to operate in the second mode by delaying the electrical stimulation therapy by:
withholding automatic delivery of the electrical stimulation therapy in response to detecting the tachyarrhythmia during the second mode;
receiving via the telemetry circuit a therapy command from an external device to schedule the electrical stimulation therapy; and
schedule the electrical stimulation therapy in response to receiving the therapy command.

9. The device of claim 1, wherein the control circuit is further configured to switch to the second mode by adjusting a monitoring parameter used by the control circuit to detect a change in a patient condition.

10. The device of claim 9, further comprising a sensor for sensing a physiological signal different than the cardiac electrical signal;
wherein the control circuit is configured to adjust the monitoring parameter by adjusting a parameter used to detect the patient condition from the physiological signal.

11. The device of claim 10, wherein the sensor comprises at least one of a temperature sensor, an impedance sensor, a pressure sensor, an acoustical sensor, an accelerometer, or an oxygen sensor.

12. The device of claim 1, wherein the control circuit is further configured to:
control the telemetry circuit to transmit a tachyarrhythmia detection signal to the ventricular assist device in response to detecting the tachyarrhythmia after switching to the second mode.

13. The device of claim 1, wherein the control circuit is configured to adjust the at least one control parameter by adjusting a cardiac pacing control parameter.

14. The device of claim 13, wherein adjusting the cardiac pacing control parameter comprises disabling left ventricular pacing.

15. The device of claim 13, wherein adjusting the cardiac pacing control parameter comprises enabling right ventricular pacing.

16. The device of claim 1, wherein the control circuit is configured to:
receive a second command indicating that the ventricular assist device is no longer co-implanted with the implantable medical device in the patient; and
restore the first mode of operating only in response to receiving the second command.

17. The device of claim 1, wherein the control circuit is configured to:
receive a periodic signal that confirms that the ventricular assist device is co-implanted with the implantable medical device in the patient; and
restore the first mode of operating in response to not receiving the periodic signal.

18. A method performed by an implantable medical device, comprising:
operating, with a control circuit of the implantable medical device, the implantable medical device according to a first mode that comprises:
detecting, with a sensing circuit of the implantable medical device, a cardiac arrhythmia from a cardiac electrical signal, and
automatically delivering, with a therapy delivery circuit of the implantable medical device, an electrical stimulation therapy to a heart of a patient in response to detecting the cardiac arrhythmia,
receiving, with a telemetry circuit of the implantable medical device, a command from another medical device indicating co-implantation of a ventricular assist device with the implantable medical device in the patient; and
switching, with the control circuit of the implantable medical device, from the first mode of operating to a second mode of operating in response to receiving the command, wherein switching from the first mode to the second mode comprises adjusting at least one control parameter used for controlling the electrical stimulation therapy and operating in the second mode, with the control circuit of the implantable medical device, by:
detecting a tachyarrhythmia from the cardiac electrical signal;
delaying the electrical stimulation therapy in response to detecting the tachyarrhythmia; and
generating an alert indicating that the tachyarrhythmia is detected and the electrical stimulation therapy is delayed.

19. The method of claim 18, wherein adjusting the at least one control parameter, with the control circuit of the implantable medical device, comprises disabling automatic delivery of the electrical stimulation therapy in response to detecting the cardiac arrhythmia during the second mode of operating.

20. The method of claim 18, further comprising adjusting the control parameter, with the control circuit of the implantable medical device, by scheduling the electrical stimulation therapy to occur at a scheduled time of day in response to detecting the cardiac arrhythmia during the second mode of operating.

21. The method of claim 18, wherein automatically delivering the electrical stimulation therapy, with the therapy delivery circuit of the implantable medical device, comprises automatically delivering a shock therapy in response to detecting the first ventricular tachyarrhythmia episode, the method further comprising:
   detecting, with the control circuit of the implantable medical device, a second ventricular tachyarrhythmia episode from the cardiac electrical signal after switching to the second mode; and
   in response to detecting the second ventricular tachyarrhythmia episode during the second mode, delaying the electrical stimulation therapy by withholding the shock therapy.

22. The method of claim 18, wherein adjusting the at least one control parameter, with the control circuit of the implantable medical device, comprises adjusting an anti-tachycardia pacing therapy control parameter.

23. The method of claim 18, wherein adjusting the at least one control parameter, with the control circuit of the implantable medical device, comprises adjusting a tachyarrhythmia detection control parameter that prolongs a minimum time required to detect a tachyarrhythmia during the second mode compared to the first mode.

24. The method of claim 18, wherein switching to the second mode, with the control circuit of the implantable medical device, further comprises adjusting criteria for generating an alert during the second mode.

25. The method of claim 18, further comprising operating according to the second mode, with the control circuit of the implantable medical device, by delaying the electrical stimulation therapy by:
   withholding automatic delivery of the electrical stimulation therapy in response to detecting the tachyarrhythmia during the second mode;
   receiving via the telemetry circuit a therapy command from an external device to schedule the electrical stimulation therapy; and
   scheduling the electrical stimulation therapy in response to receiving the therapy command.

26. The method of claim 18, wherein switching to the second mode, with the control circuit of the implantable medical device, further comprises adjusting a monitoring parameter for detecting a change in a patient condition.

27. The method of claim 26, further comprising sensing, with a sensor of the implantable medical device, a physiological signal different than the cardiac electrical signal;
   wherein adjusting the monitoring parameter, with the control circuit of the implantable medical device, comprises adjusting a parameter used to detect the patient condition from the physiological signal.

28. The method of claim 27, wherein sensing the physiological signal, with the sensor of the implantable medical device, comprises sensing at least one of a temperature signal, an impedance signal, a pressure signal, an acoustical signal, an accelerometer signal, or an oxygen signal.

29. The method of claim 18, further comprising:
   transmitting, with the telemetry circuit of the implantable medical device, a tachyarrhythmia detection signal to the ventricular assist device in response to detecting, with the control circuit of the implantable medical device, the tachyarrhythmia after switching to the second mode.

30. The method of claim 18, wherein adjusting the at least one control parameter, with the control circuit of the implantable medical device, comprises adjusting a cardiac pacing control parameter.

31. The method of claim 30, wherein adjusting the cardiac pacing control parameter, with the control circuit of the implantable medical device, comprises disabling left ventricular pacing.

32. The method of claim 30, wherein adjusting the cardiac pacing control parameter, with the control circuit of the implantable medical device, comprises enabling right ventricular pacing.

33. The method of claim 18, further comprising
   receiving, with the telemetry circuit of the implantable medical, a second command indicating that the ventricular assist device is no longer co-implanted with the implantable medical device in the patient; and
   restoring, with the control circuit of the implantable medical device, the first mode of operating only in response to receiving the second command.

34. The method of claim 18, further comprising:
   receiving, with the telemetry circuit of the implantable medical, a periodic signal that confirms that the ventricular assist device is co-implanted with the implantable medical device in the patient; and
   restoring, with the control circuit of the implantable medical device, the first mode of operating in response to not receiving the periodic signal.

35. A non-transitory, computer-readable storage medium comprising a set of instructions which, when executed by a controller of an implantable medical device, cause the device to:
   operate according to a first mode that comprises:
      detecting a cardiac arrhythmia from a cardiac electrical signal, and
      automatically delivering an electrical stimulation therapy to a heart of a patient in response to detecting the cardiac arrhythmia,
   receive a command from another medical device indicating co-implantation of a ventricular assist device with the implantable medical device in the patient; and
   switch from the first mode of operating to a second mode of operating in response to receiving the command, wherein switching from the first mode to the second mode comprises adjusting at least one control parameter used for controlling the electrical stimulation therapy and wherein operating in the second mode comprises:
      detecting a tachyarrhythmia from the cardiac electrical signal;
      delaying the electrical stimulation therapy in response to detecting the tachyarrhythmia; and
      generating an alert indicating that the tachyarrhythmia is detected and the electrical stimulation therapy is delayed.

36. An implantable medical device comprising:
   a sensing circuit configured to receive a cardiac electrical signal produced by a heart of a patient;
   a therapy delivery circuit configured to generate an electrical stimulation therapy for delivery to the heart of the patient;

a telemetry circuit configured to receive a command from another medical device indicating co-implantation of a ventricular assist device with the implantable medical device in the patient; and a control circuit coupled to the sensing circuit, the therapy delivery circuit and the telemetry circuit and configured to:

operate in a first mode comprising detecting a cardiac arrhythmia from the cardiac electrical signal as a first ventricular tachyarrhythmia episode and controlling the therapy delivery circuit to automatically deliver the electrical stimulation therapy as a shock therapy in response to detecting the first ventricular tachyarrhythmia episode; and switch from operating in the first mode to operating in a second mode in response to receiving the command, wherein switching to the second mode comprises adjusting at least one control parameter used for controlling the electrical stimulation therapy, detect a second ventricular tachyarrhythmia episode from the cardiac electrical signal after switching to the second mode; and in response to detecting the second ventricular tachyarrhythmia episode during the second mode, withhold the shock therapy.

* * * * *